(12) United States Patent
Navon et al.

(10) Patent No.: US 9,554,991 B2
(45) Date of Patent: *Jan. 31, 2017

(54) CARBIDOPA/LEVODOPA GASTRORETENTIVE DRUG DELIVERY

(71) Applicant: INTEC PHARMA LTD., Jerusalem (IL)

(72) Inventors: Nadav Navon, Rehovot (IL); Eytan Moor, Jerusalem (IL); David Kirmayer, Maale Adumim (IL); Elena Kluev, Jerusalem (IL); Giora Carni, Tel Aviv (IL)

(73) Assignee: INTEC PHARMA LTD., Jerusalem (IL)

( * ) Notice: Subject to any disclaimer, the term of this patent is extended or adjusted under 35 U.S.C. 154(b) by 0 days.

This patent is subject to a terminal disclaimer.

(21) Appl. No.: 14/995,611

(22) Filed: Jan. 14, 2016

(65) Prior Publication Data

US 2016/0199300 A1    Jul. 14, 2016

Related U.S. Application Data

(63) Continuation of application No. 14/715,077, filed on May 18, 2015, now Pat. No. 9,259,387, which is a continuation of application No. 14/322,436, filed on Jul. 2, 2014, now Pat. No. 9,072,663, which is a continuation of application No. 12/937,955, filed as application No. PCT/IB2009/005691 on Apr. 17, 2009, now Pat. No. 8,771,730.

(60) Provisional application No. 61/120,051, filed on Dec. 4, 2008, provisional application No. 61/046,261, filed on Apr. 18, 2008.

(51) Int. Cl.
| | |
|---|---|
| *A61K 9/48* | (2006.01) |
| *A61K 9/00* | (2006.01) |
| *A61K 9/70* | (2006.01) |
| *A61K 9/28* | (2006.01) |
| *A61K 31/198* | (2006.01) |
| *A61K 45/06* | (2006.01) |
| *A61K 31/195* | (2006.01) |

(52) U.S. Cl.
CPC .......... *A61K 9/0065* (2013.01); *A61K 9/2886* (2013.01); *A61K 9/48* (2013.01); *A61K 9/4808* (2013.01); *A61K 9/4866* (2013.01); *A61K 9/4875* (2013.01); *A61K 9/7007* (2013.01); *A61K 31/195* (2013.01); *A61K 31/198* (2013.01); *A61K 45/06* (2013.01)

(58) Field of Classification Search
None
See application file for complete search history.

(56) References Cited

U.S. PATENT DOCUMENTS

| | | |
|---|---|---|
| 4,767,627 A | 8/1988 | Caldwell et al. |
| 6,485,746 B1 | 11/2002 | Campbell et al. |
| 6,605,300 B1 | 8/2003 | Burnside et al. |
| 6,685,962 B2 | 2/2004 | Friedman et al. |
| 8,771,730 B2 | 7/2014 | Navon et al. |
| 9,072,663 B2 | 7/2015 | Navon et al. |
| 2003/0013726 A1 | 1/2003 | Selzer |
| 2003/0021845 A1 | 1/2003 | Friedman et al. |
| 2003/0118640 A1 | 6/2003 | Dash |
| 2004/0180088 A1 | 9/2004 | Dudhara et al. |
| 2005/0136109 A1 | 6/2005 | Rowley et al. |
| 2005/0244517 A1 | 11/2005 | Hall et al. |
| 2006/0024365 A1 | 2/2006 | Vaya et al. |
| 2007/0281007 A1 | 12/2007 | Jacob et al. |
| 2008/0020039 A1 | 1/2008 | Parikh et al. |
| 2010/0305208 A1 | 12/2010 | Dudhara et al. |
| 2012/0021051 A1 | 1/2012 | Masri et al. |
| 2012/0288551 A1 | 11/2012 | Tabuteau |
| 2014/0017303 A1 | 1/2014 | Navon et al. |

FOREIGN PATENT DOCUMENTS

| | | |
|---|---|---|
| CN | 1520286 A | 8/2004 |
| JP | H103163011 | 7/1991 |
| WO | 0100181 A2 | 1/2001 |
| WO | 06072948 A2 | 7/2006 |
| WO | 2007/083309 A2 | 7/2007 |
| WO | 2007/093999 A1 | 8/2007 |
| WO | 2008110577 A1 | 9/2008 |
| WO | 2009144558 A1 | 12/2009 |
| WO | 2010019915 A1 | 2/2010 |

OTHER PUBLICATIONS

International Search Report and Written Opinion for International Application No. PCT/182009/005691, dated Oct. 20, 2009, 17 pages.
Tom et al., "Applications of Supercritical Fluids in the Controlled Release of Drugs", Supercritical Fluid Engineering Science, 19:238-257, ACS Symposium Series vol. 514 (1962).
Morris et al., "Effects of Written Drug Information on Patient Knowledge and Compliance: A Literature Review" Am J Public Health 69(1):47-52 (1979).
Copy of the Office Action received in the related U.S. Appl. No. 12/797,441, dated May 22, 2012.
Whishead et al. "Development of Gastrorententive Dosage Form." Eur. J. Pharm. Sci. 4.S1 (1996):S182. (Abstract #P3.069).

(Continued)

*Primary Examiner* — Hasan Ahmed
(74) *Attorney, Agent, or Firm* — Browdy and Neimark, PLLC

(57) ABSTRACT

A gastroretentive drug formulation for the sustained release of an active agent in the gastrointestinal tract comprises an internal layer or compartment comprising an active agent and one or more pharmaceutical excipients, of which at least one is a polymer and two membranes forming together an envelope around the inner membrane, each membrane comprising at least one polymeric combination of an enteric polymer which is not soluble in gastric juice, and an hydrophilic swelling polymer, and at least one plasticizer.

26 Claims, 13 Drawing Sheets

(56) References Cited

OTHER PUBLICATIONS

Moes. "Gastroretentive Dosage Forms." Grit. Rev. Ther. Drug CarrierSyst. 10.2(1993):143-195.
Jimenez-Castellanos et al. "Mucoadhesive Drug Delivery Systems." Drug Dev. Industr. Pharmacy. 19.1&2 (1993)143-194.
Iannuccelli et al. "Air Compartment Multiple-Unit System for Prolonged Gastric Residence. Part II. In vivo Evaluation." Int. J. Pharm. 174(1-2)55-62(1998).
Hwang et al. "Gastric Retentive Drug-Delivery Systems." Crit. Rev. Ther. Drug Carrier Syst. 15.3:243-284 (1998).
Desai et al. "A Floating Controlled-Release Drug Delivery System: In Vitro-In Vivo Evaluation." Pharm. Res. 10.9:1321-1325 (1993).
Goetz et al. "Movement Disorder Society-Sponsored Revision of the Unified Parkinson's Disease Rating Scale (MDS-UPSRD): Process, Format, and Clinimetric Testing Plan" Movement Disorders. 22.1:41-47 (2007).
Danjou, et al. "A comparison of the residual effects of zaleplon and zolpidem following administration 5 to 2 h before awakening", J Clin Pharmacal, 48:367-374 (1999).

A DRAWING OF THE CURRENT GRDF DESIGN SHOWING THE
PLANAR DIMENSIONS OF THE WHOLE GRDF AND OF THE INNER LAYER

A DRAWING SHOWING THE PLACEMENT OF A SINGLE IMMEDIATE RELEASE
LAYER ON TOP OF THE OUTER IN A CROSS SECTION VIEW (A). AS SHOWN IN B, THE
IMMEDIATE RELEASE LAYER COVERS THE ENTIRE SURFACE OF THE GRDF

A SCHEMATIC DRAWING OF THE FILM
COMPONENTS OF A GRDF WITH AN IMMEDIATE RELEASE
LAYER AND THEIR APPROXIMATE DIMENSIONS

A PHOTOGRAPH SHOWING A GRDF FOLDED INSIDE CAPSULE PRIOR
TO PLACING THE CAPSULE CAP. VISIBLE ARE THE FOLDS AND THEIR FOLD
GEOMETRY.

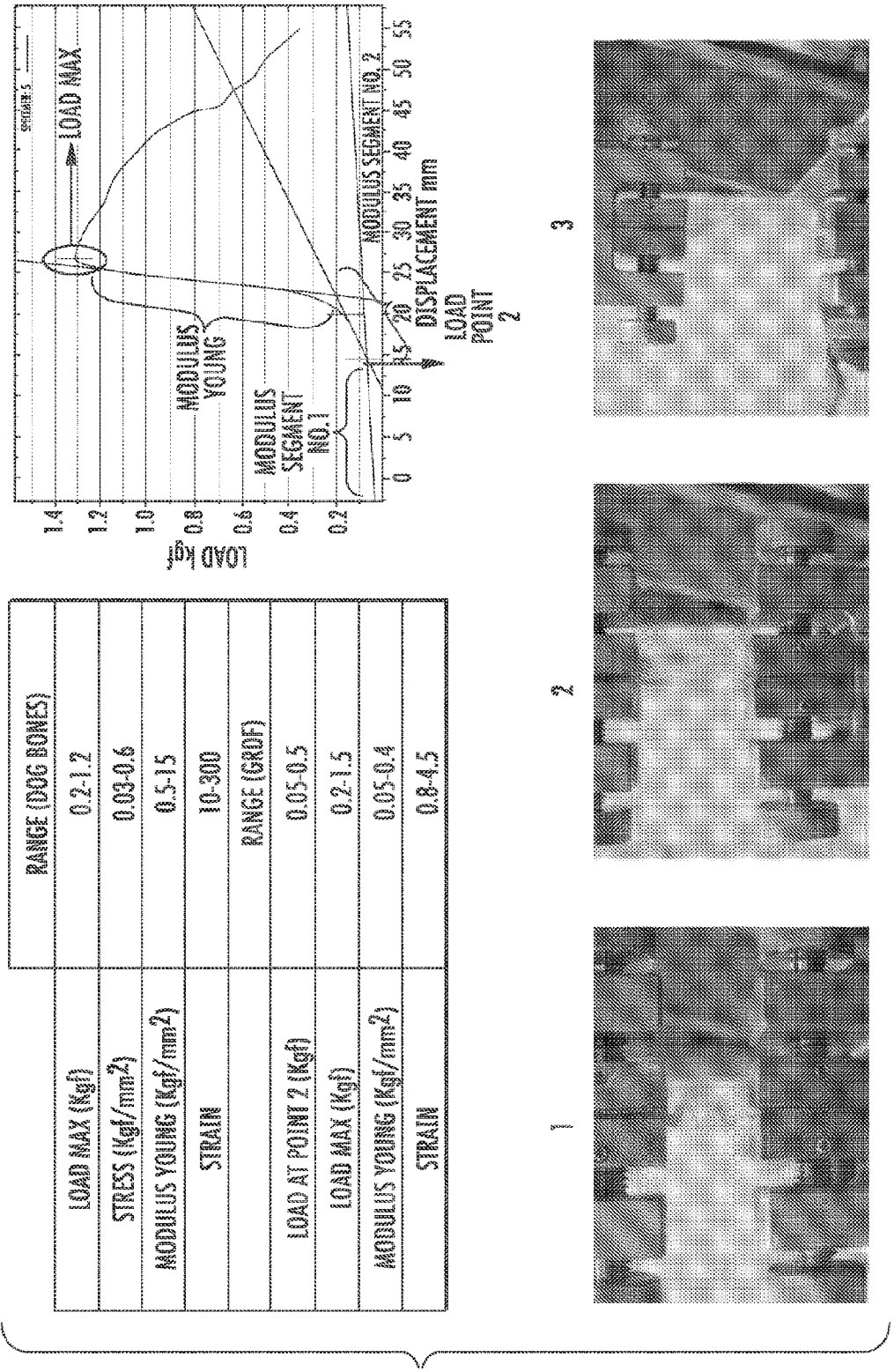

A DRAWING SHOWING THE DESIGN OF THE ANVIL (A) AND HORN OF (B) THE ULTRASOUND WELDING MACHINE USE FOR ATTACHING THE GRBF LAYERS TOGETHER.

A DRAWING OF THE ULTRASOUND WELDING ON THE GRDF (A).
THE PERIMETER LINE OF THE INNER IS SHOWN WITH AN ARROW AND THE
EXTENT OF WELDING IN A CROSS SECTION OF THE GRDF IS PROVIDED (B).

AN ENLARGED PHOTOGRAPH OF A PART GRDF SHOWING THE ULTRASOUND WELDING OF THE PERIMETER (OUTER TO OUTER) SEALING THE ENVELOPE AND THE MORE CENTRAL WELDING OF THE OUTER TO THE INNER FILM.

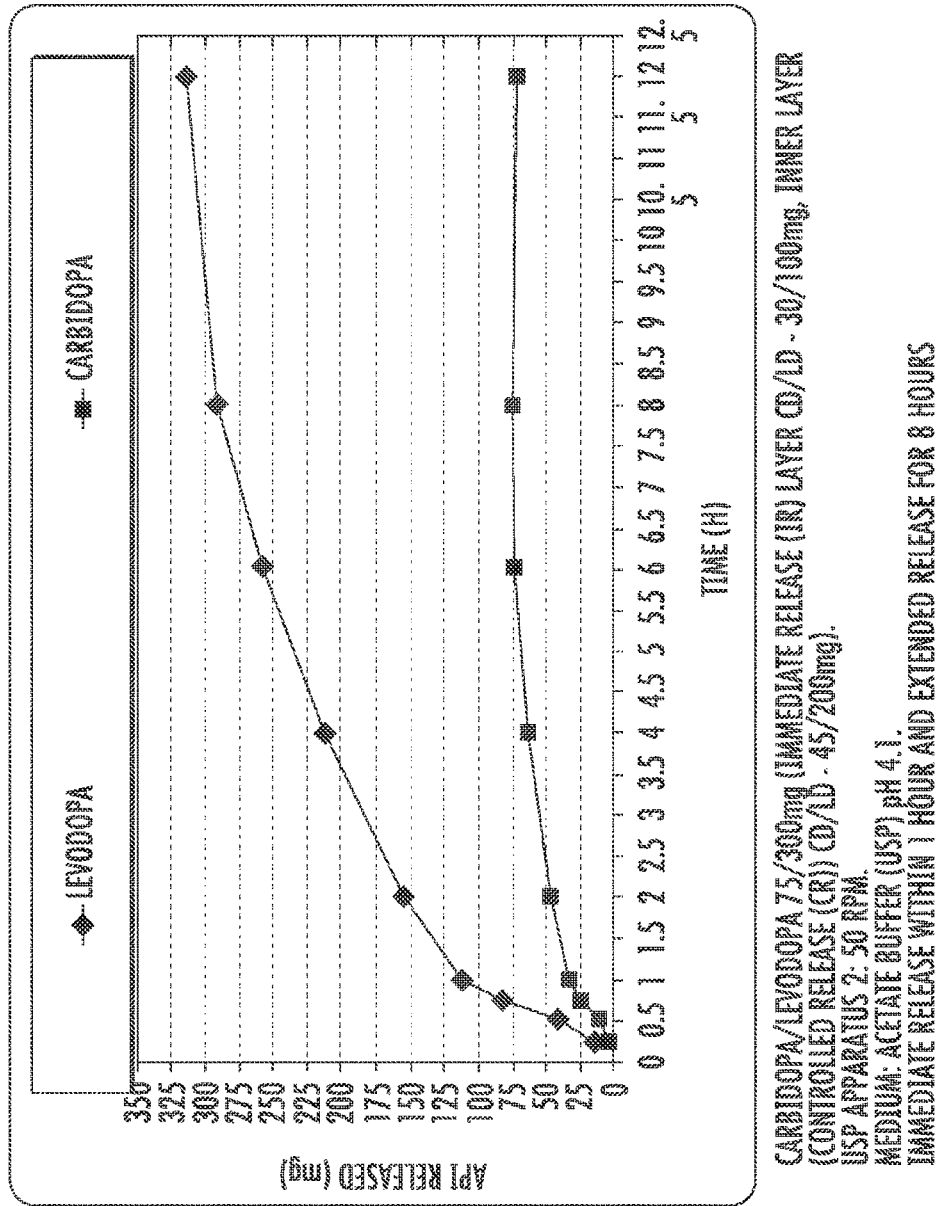

FIGURE 10 - UNFOLDING OF PLACEBO CRID

MEDIUM: SGF pH 1.2 AND ACETATE BUFFER (USP) pH 4.1.
TIME: 15 (VISUAL INSPECTION), 30, 60 AND 120 MINUTES.
USP APPARATUS 2; 50 RPM.

| TIME (MINUTES) | 1 | 2 | 3 | 4 | MEAN | STDEV | RSD |
|---|---|---|---|---|---|---|---|
| pH 4.1 UNFOLDING (mm) | 30 | | | | | | |
| | 30 | 30.8 | 32.0 | 30.5 | 33.5 | 31.7 | 1.41 | 4% |
| | 60 | 30.4 | 32.6 | 31.1 | 34.1 | 32.1 | 1.65 | 5% |
| | 120 | 32.2 | 35 | 33.3 | 34.8 | 33.8 | 1.32 | 4% |
| UNFOLDING (%) | 30 | 68 | 71 | 69 | 74 | 70.3 | 3.13 | 4% |
| | 60 | 66 | 72 | 69 | 76 | 71.2 | 3.66 | 5% |
| | 120 | 72 | 78 | 74 | 77 | 75.2 | 2.94 | 4% |

| TIME (MINUTES) | 1 | 2 | 3 | 4 | MEAN | STDEV | RSD |
|---|---|---|---|---|---|---|---|
| pH 1.2 UNFOLDING (mm) | 30 | 34.3 | 33.7 | 31.3 | 32.7 | 33.1 | 1.23 | 4% |
| | 60 | 34.4 | 33.4 | 32.1 | 32.2 | 33.0 | 1.09 | 3% |
| | 120 | 33.1 | 31.3 | 33.6 | 33.6 | 32.9 | 1.09 | 3% |
| UNFOLDING (%) | 30 | 76 | 75 | 70 | 73 | 73.4 | 2.72 | 4% |
| | 60 | 76 | 74 | 71 | 72 | 73.4 | 2.42 | 3% |
| | 120 | 74 | 70 | 75 | 75 | 73.1 | 2.43 | 3% |

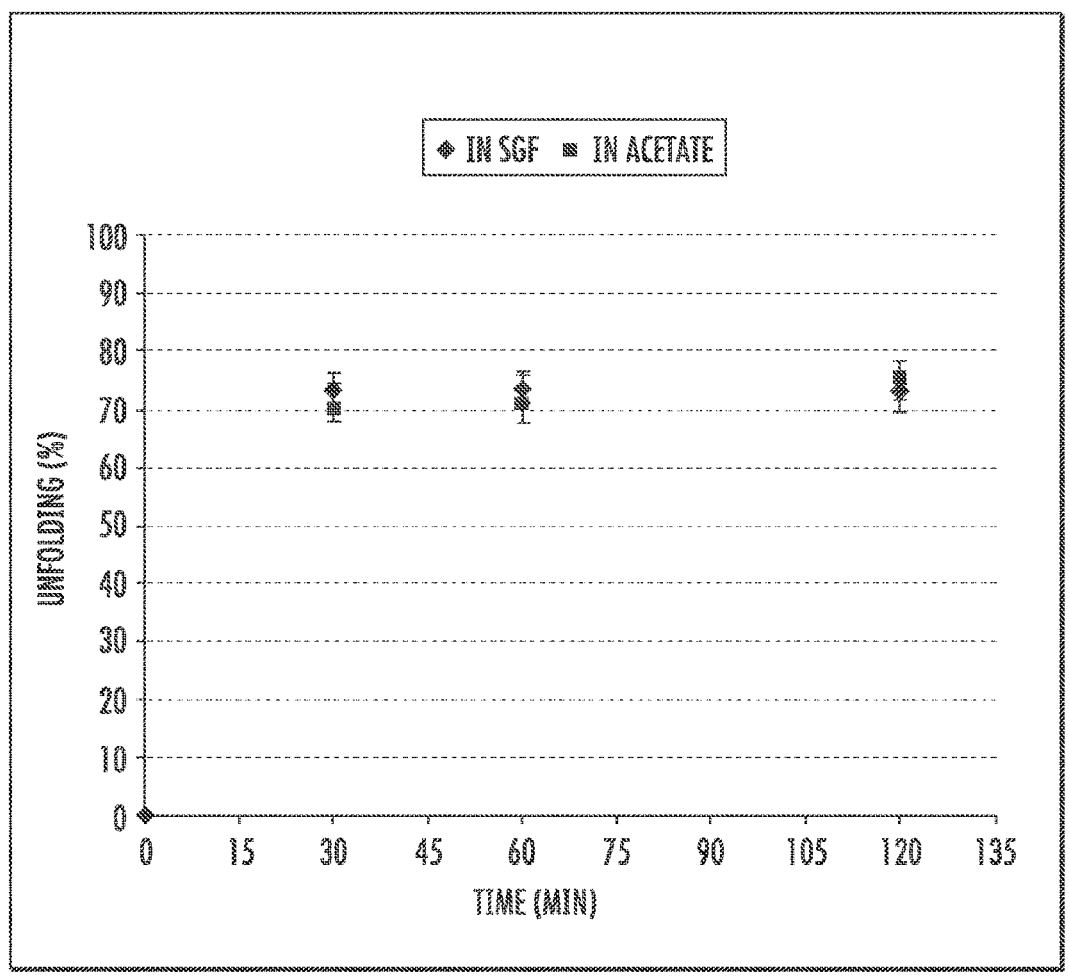

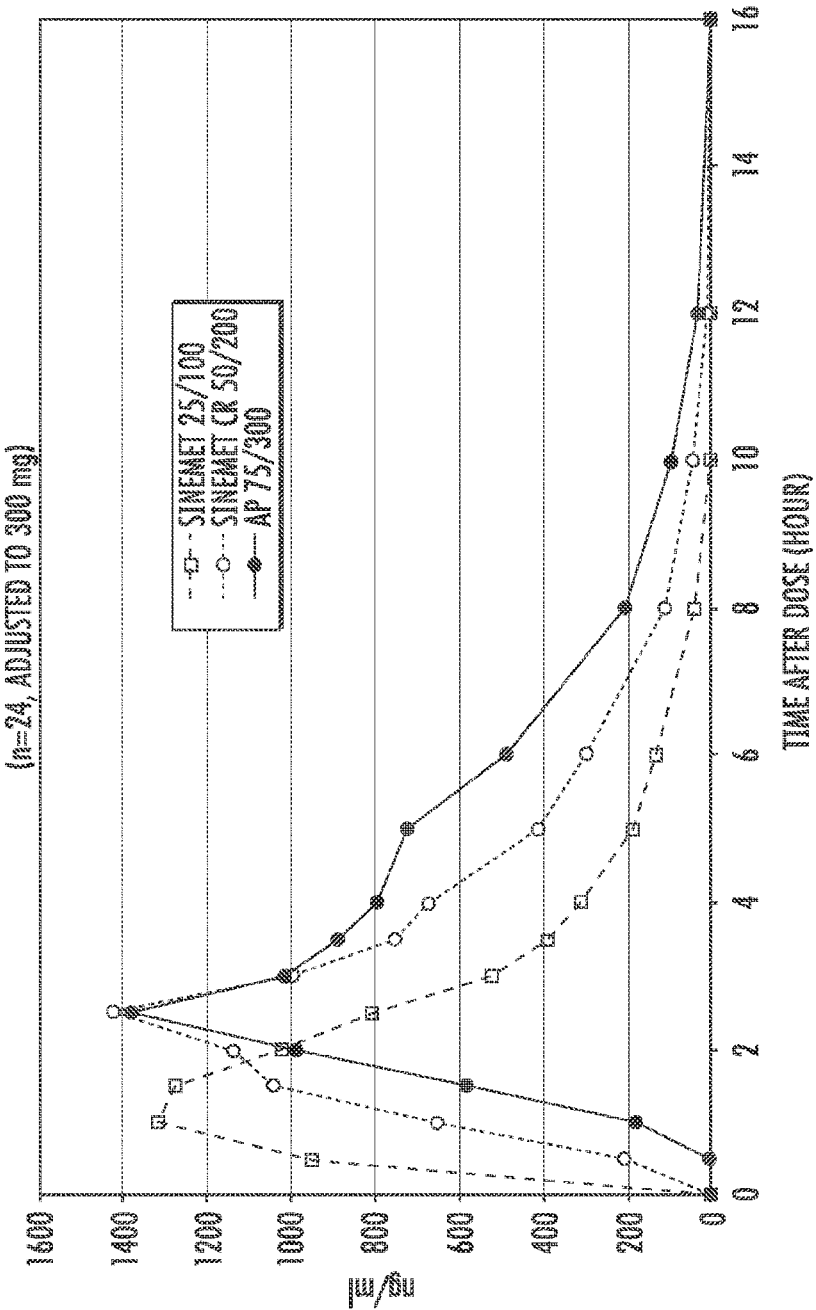

CARBIDOPA/LEVODOPA GASTRORETENTIVE DRUG DELIVERY

CROSS-REFERENCE TO RELATED APPLICATIONS

The present application claims priority to U.S. Provisional Patent Applications Nos. 61/046,261, filed on Apr. 18, 2008, and 61/120,051, filed Dec. 4, 2008, and which are incorporated herein by reference in their entirety.

FIELD OF THE INVENTION

The present invention is related to multi-layered, biodegradable gastroretentive drug formulations for the controlled release of active pharmaceutical agents with a narrow absorption window in the upper gastrointestinal tract, that act locally in the gastrointestinal tract, or that possess other rationales for gastric retentive administration. Further, the invention describes multi-layered, biodegradable gastroretentive drug formulations for the immediate release and sustained release of such active agents. The gastroretentive drug formulations of the invention may be administered orally to a mammal for the systemic or local treatment of a pathologic condition or deficiency.

BACKGROUND OF THE INVENTION

Administration of some drugs, such as amino and nucleic acid analogs, peptides peptidomimetic drugs, various antibiotics, various anti-viral drugs, and some others, to a mammal, results in delivery to gastrointestinal tract and absorption of these drugs only in specific regions of the gastrointestinal tract, like the stomach, duodenum and small intestine, such that only drugs delivered to proximity of these regions are absorbed. This phenomenon is frequently referred to as "narrow absorption window" (NAW). Various other drugs' action sites are located in specific regions of the gastrointestinal tract. In addition, various other drugs, such as water-insoluble drugs, possess pharmaceutical rationales for gastric retentive administration. Moreover, the transit time through every region of gastrointestinal tract is a highly variable value.

Despite the advances in sustained release technology for many drugs, controlled release of drugs having a relatively narrow absorption window in the gastrointestinal tract remains a challenge. A need exists to extend the gastric residence time for these drugs, so that the drug is released into the proximity of its site of absorption (or action) for an extended period, or reaches other sites of the GI tract in a uniform manner. Examples of delivery systems capable of increasing the residence time of a drug are floating low-density dosage forms, such as so-called hydrodynamically-balanced delivery systems, effervescent systems comprising gas-generating materials. Also other delivery systems, such as high-density dosage forms and bioadhesive or mucoadhesive formulations that slow upper GI transit by adhering to the intestinal mucosa have been attempted (Hwang, S J. et al., *Critical Reviews in Therapeutic Drug Carrier Systems*, 15 (3): 243-84 (1998); Desai, S. and Bolton, S., *Pharmac. Res.* 10 (9): 1321-25 (1993); Whitehead, L. et al., *European J. Pharm. Sci.*, 4 (1): S182 (1996); Iannuccelli, V. et al., *Intern. J. Pharmac.* 174: 55-62 (1998); Jimenez-Castellanos, N R. et al., *Drug Develop. Industr. Pharmacy* 19: 143 (1993); Moës, A J. *Crit. Rev. Ther. Drug Carrier Syst.* 10(2): 143-195 (1993)).

Controlled-release (CR) drug formulations present the advantage of delivering the drug of interest over a prolonged time intervals and eliminating the inconvenience of repetitive daily dosages with concomitant side effects. However, conventional CR drug delivery systems are seldom suitable for drugs with a relatively narrow absorption window in the gastrointestinal tract, since their residence time in or above the absorption window is shorter than the release time span that could be deemed beneficial. Thus, there is a need in the art for controlled-release drug formulations that provide sustained release of drugs having a relatively narrow absorption window in the gastrointestinal tract. Similarly, it is deemed beneficial in certain instances to establish therapeutic blood levels quickly and sustain them over longer periods, the subject known in the art as "the loading dose", and there is a need in the art for a combined drug formulation comprising an immediate release component and a sustained release component suitable for delivery of narrow-absorption window substances. U.S. Pat. No. 6,685,962 B2, incorporated herein by reference, provides pharmaceutical gastroretentive drug delivery systems for the controlled release of an active agent in the gastrointestinal tract.

The present invention satisfies the need in the art for formulations that provide sustained release or combined immediate release and sustained release of drugs with a narrow absorption window in the gastrointestinal tract, or other rationales for a gastroretentive administration, by providing gastroretentive drug formulations that are also completely biodegradable, and with a relatively high loading capacity.

SUMMARY OF THE INVENTION

Further to these objects, the invention provides biodegradable, multi-layered gastroretentive drug formulations for the sustained release of an active agent in the gastrointestinal tract. In another aspect, the invention provides biodegradable, multi-layered gastroretentive drug formulations for combined immediate release and sustained release of an active agent in the gastrointestinal tract.

In one embodiment, a biodegradable, multi-layered gastroretentive drug formulation for the sustained release of an active agent in the stomach and gastrointestinal tract of a patient, includes an internal layer containing an active agent and a degradable polymer which is not instantly soluble in gastric fluid. The internal layer includes a first side and an opposing second side. At least one membrane is covering the internal layer. The membrane comprises at least one polymeric combination of a hydrophilic polymer and a polymer, insoluble in gastric media, the membrane being hydratable in the gastric media. The membrane is directly secured to and covers both sides of the internal layer and has a predetermined length greater than 20 mm in a planar orientation, the membrane and internal layer being arranged in an accordion folded orientation sufficiently compact to be placed within a capsule dissolvable within the stomach of a patient and simulated gastric media. The membrane and internal layer unfold from the accordion folded orientation to a length of at least 20 mm within 30 minutes of being exposed to gastric media. The membrane permits passage of gastric media from the environment to the internal layer and permits passage of the active agent from the internal layer through the membrane to the environment.

In another embodiment, a biodegradable, multi-layered gastroretentive drug formulation for the sustained release of an active agent in the gastrointestinal tract, includes an internal layer comprising an active agent and a degradable polymer which is not instantly soluble in gastric fluid. A first and second membranes cover the internal layer, the membranes including at least one polymeric combination of a hydrophilic polymer and a polymer, insoluble in gastric media and the membranes being hydratable. The first and second membranes are having a width and length greater than a width and length of the internal layer. The first and second membranes are being ultrasonically welded or otherwise affixed or attached directly together about the periphery of the first and second membranes. The first membrane is being ultrasonically welded to a first side of the internal layer, the second membrane is being ultrasonically welded to the second side of the internal layer. The ultrasonically welded internal layer and first and second membranes have a predetermined length greater than 20 mm in a planar orientation, the membrane and internal layer being arranged in an accordion folded orientation sufficiently compact to be placed within a capsule dissolvable within the stomach or simulated gastric media. The ultrasonic welds having sufficient mechanical strength and stability to remain intact when being exposed to gastric fluid.

In still another embodiment, a biodegradable, multi-layered gastroretentive drug formulation for the sustained release of an active agent in the gastrointestinal tract is disclosed, including an internal layer comprising an active agent and a degradable hydrophilic polymer which is not instantly soluble in gastric fluid and a degradable enteric polymer which is substantially insoluble at pH less than 5.5, and optionally a plasticizer. At least one membrane covers the internal layer, the membrane includes at least one polymeric combination of a hydrophilic polymer and a polymer, insoluble in gastric media, and at least one plasticizer. The membranes swell in the presence of gastric fluid. At least one of the materials in each of the internal layer and membranes are being capable of being ultrasonically welded together. The membrane is directly secured to and covers both sides of the internal layer and has a predetermined length greater than 20 mm in a planar orientation. The membrane and internal layer are being arranged in an accordion folded orientation sufficiently compact to be placed within a capsule dissolvable within the stomach or in simulated gastric media. The membrane permits passage of gastric media from the environment to the internal layer and permits passage of the active agent from the internal layer through the membrane to the environment. The membrane and internal layer unfold from the accordion folded orientation to a length of at least 20 mm within 30 minutes of being exposed to gastric fluid.

In still another embodiment a biodegradable, multi-layered gastroretentive drug formulation for the sustained release of an active agent in the gastrointestinal tract includes an internal layer comprising an active agent and a degradable hydrophilic polymer which is not instantly soluble in gastric fluid and a degradable enteric polymer which is substantially insoluble at pH less than 5.5, and a plasticizer. First and second membranes cover the internal layer, the membranes include at least one polymeric combination of a hydrophilic polymer and a polymer, insoluble in gastric media, and at least one plasticizer. The membranes swell in the presence of gastric fluid. At least one of the materials in each of the internal layer and membranes are being capable of being ultrasonically welded together. The membranes being directly secured to and covering both sides of the internal layer and having a predetermined length greater than 20 mm in a planar orientation, the membranes and internal layer being arranged in an accordion folded orientation sufficiently compact to be placed within a capsule dissolvable within the stomach. The membranes and internal layer unfold from the accordion folded orientation to a length of at least 20 mm within 30 minutes of being exposed to gastric fluid. The first and second membranes have a width and length greater than a width and length of the internal layer. The first and second membranes are ultrasonically welded or otherwise affixed or attached directly together about a periphery of the first and second membranes. The first membrane is ultrasonically welded to a first side of the internal layer. The second membrane is ultrasonically welded to the second side of the internal layer. The membrane permits passage of gastric media from the environment to the internal layer and permits passage of the active agent from the internal layer through the membrane to the environment. The ultrasonically welded internal layer and first and second membranes have a predetermined length greater than 20 mm in a planar orientation. The membrane and internal layer being arranged in an accordion folded orientation sufficient to be placed within a capsule dissolvable within the stomach. The ultrasonic welds having sufficient mechanical strength and stability to remain intact when being exposed to gastric fluid.

In one embodiment, the gastroretentive drug formulations are for the sustained release of an active agent in the gastrointestinal tract and comprise: i.) an internal layer or compartment comprising the active agent and one or more pharmaceutical excipients, of which at least one is a polymer, ii.) two membranes forming together an envelope around the inner membrane, each comprising at least one polymeric combination of a polymer which is not soluble in gastric juice, and a hydrophilic swelling polymer, and at least one plasticizer; and iii.) optionally an additional layer covering each outer membrane comprising a powder or a film that prevents adherence of the outer membrane onto itself when folded inside the capsule.

In a different embodiment, the gastroretentive drug formulations are for the immediate release and the sustained release of an active agent in the gastrointestinal tract and comprise: i.) an internal layer or compartment comprising the active agent and a polymer; ii.) two membranes forming together an envelope around the inner membrane, each comprising at least one polymeric combination of a polymer which is not soluble in gastric juice, and a hydrophilic swelling polymer, and at least one plasticizer; and iii.) one or two layers comprising the active agent and a soluble polymer that provides for the immediate release of the active agent and is attached to the outside of one outer membrane or both outer membranes or part of an outer membrane. Optionally an additional layer may be covering each immediate release membrane comprising a powder or a film that prevents adherence of the outer membrane or IR membrane onto itself when folded inside the capsule. In some embodiments, the immediate-release membranes possess surface properties that prevent adherence onto itself when folded inside the capsule.

In preferred embodiments, the gastroretentive drug formulations effectively unfold and retain their mechanical integrity in acidic pH for up to 24 hours and completely biodegrade after 3 hours in simulated intestinal fluid.

In one aspect, the polymer in the internal layer is a degradable polymer which is not instantly soluble in gastric fluid. In another aspect, the polymer is a degradable enteric polymer which is substantially insoluble at pH less than 5.5. The invention also contemplates mixtures of polymers as described above.

In one embodiment the enteric polymer in the internal layer is polymethacrylate copolymer. In different embodiments, the enteric polymer is cellulose acetate phthalate, or hydroxypropylmethyl cellulose phthalate, or hydroxypropyl methyl cellulose acetate succinate. In a preferred embodiment, the active agent and the polymer are substantially uniformly distributed in the internal layer.

In another embodiment, the polymeric combination of the outer membranes comprises gelatin and hydroxypropyl methyl cellulose acetate succinate as enteric polymer.

In one embodiment, the enteric polymer in the outer membranes is polymethacrylate copolymer type A. In a different embodiment, the enteric polymer in the outer membranes is polymethacrylate copolymer type C. In a further embodiment, the plasticizer in the outer membranes is propylene glycol.

In a preferred embodiment, the internal layer or compartment, the outer membranes and the optional additional layers or the immediate release layers are sealed by applying ultrasonic welding.

In an additional embodiment, the internal layer provides at least 50% of the mechanical strength of the whole GRDF when wetted with gastric fluid. In a preferred embodiment, the gastroretentive drug formulation reaches its maximum strength within one hour in simulated gastric fluid. In yet another preferred embodiment, the internal layer has a planar-accordion geometry that unfolds to at least 50% of its original length within 30 minutes in gastric media.

In one aspect, the gastroretentive drug formulation is fully degradable within 3 hours in simulated intestinal fluid. In an additional aspect, the gastroretentive drug formulation provides gastric retention for up to 24 hours under low or medium calorie diet. In yet another aspect, the gastroretentive drug formulation moves in the stomach during gastric retention.

The gastroretentive drug formulations are designed for oral administration and are compacted or folded into a standard size capsule which is easily swallowed. The active ingredient or ingredients is/are incorporated in the gastroretentive drug formulations as dissolved matter in composition of the formulation, powders, grains, spheres, particles, microparticles, nanoparticles, multiparticulates, tablets or microcapsules.

In one aspect, the active agent has a narrow window of absorption in the gastrointestinal tract. The active agent can be a therapeutic nucleic acid sequence, a therapeutic protein or peptide, amino acid analogs, a peptidomimetic drug, a nucleoside analogue, an antibiotic, a therapeutic ion, a vitamin, a bronchodilator, an anti-gout agent, an anti-hypertensive agent, a diuretic agent, an anti-hyperlipidemic agent, an ACE inhibitor, an anti-tumor agent, an histamine (H2) blocker, a bismuth salt or a synthetic prostaglandin. In one aspect, the active agent is levodopa and levodopa/carbidopa mixture. Preferred antibiotic agent is selected from a beta-lactam group, and from fluoroquinolone group.

In another aspect the active agent is a drug for the local treatment in the gastrointestinal tract, such as various drugs for the treatment of local infections, or drugs for the treatment of various gastrointestinal diseases and symptoms, or drugs for the treatment of metabolic disorders, such as obesity, diabetes, hyper-cholesterol, or for the treatment of local cancers or for the treatment of cancer related diseases. In preferred aspects the drugs comprise serotonergic compounds and another enteric neuromodulators, poorly absorbed substances, poorly absorbed antibiotics and compounds, acting in the liver as primary pharmacological site.

The foregoing general description and following brief description of the drawings and the detailed description are exemplary and explanatory and are intended to provide further explanation of the invention as claimed. Other objects, advantages, and novel features will be readily apparent to those skilled in the art from the following detailed description of the invention.

BRIEF DESCRIPTION OF THE DRAWINGS

FIG. 5 provides results indicating the mechanical properties of GRDFs and films cut into a dog bone shape. The photographs marked 1, 2 and 3 show the stages of mechanical testing of a GRDF after immersion in SGF. The figure in the top right corner shows the results as expressed in a load-to-displacement graph, where the stages of the test correspond to the stages shown in photographs 1, 2 and 3, respectively.

FIG. 9 shows the dissolution profile of a combined immediate release and controlled release carbidopa/levodopa GRDF.

FIGS. 10 and 11 show the measurements from the unfolding of a placebo GRDF device in acetate buffer and SGF.

FIG. 12 shows the mean dose-adjusted Carbidopa concentrations for single dose GRDF CD/LD 75/300 mg gastric retentive, IR+CR; single dose Sinemet® IR 100/25 mg; and single dose Sinemet CR® 25/100 mg, as described in Example 7.

DETAILED DESCRIPTION OF THE INVENTION

Definitions

Figure 1:
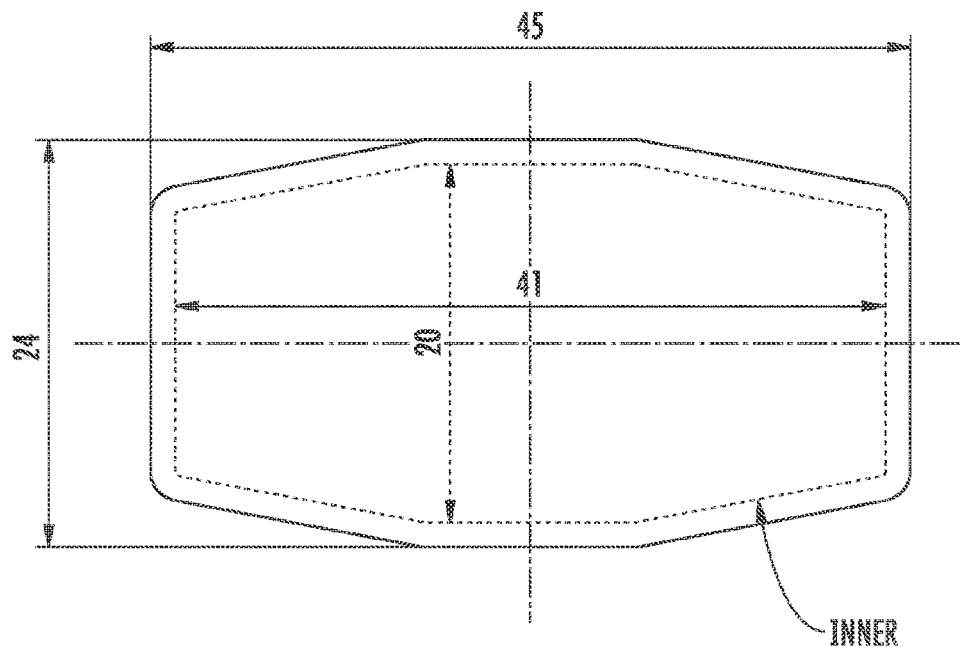
FIG. 1 shows one embodiment of the GRDF design showing the planar dimensions of the whole GRDF and of the internal layer.
Figure 2A:
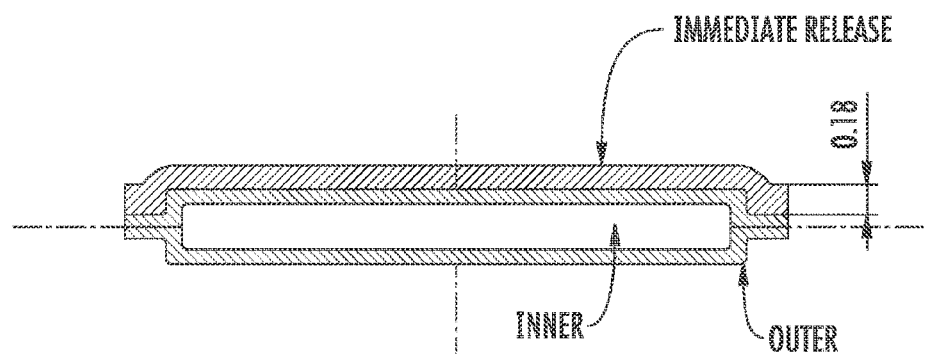
FIGS. 2A and 2B show the placement of a single immediate release layer on top of the outer membrane in a cross section view (A). As shown in (B), the immediate release layer covers the entire surface of the GRDF.
Figure 2B:
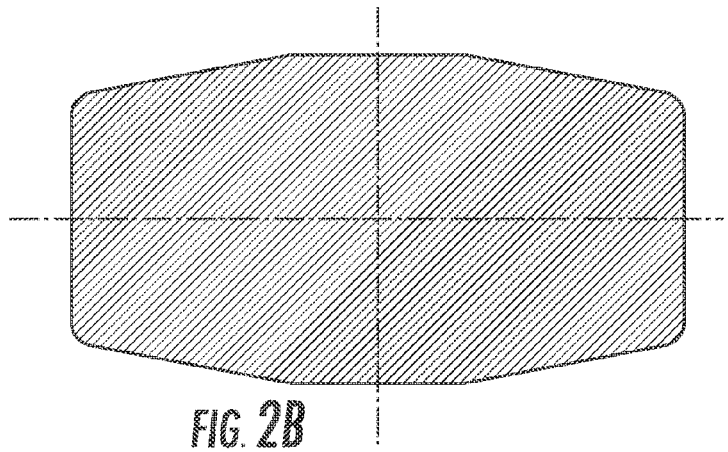
Figure 3:
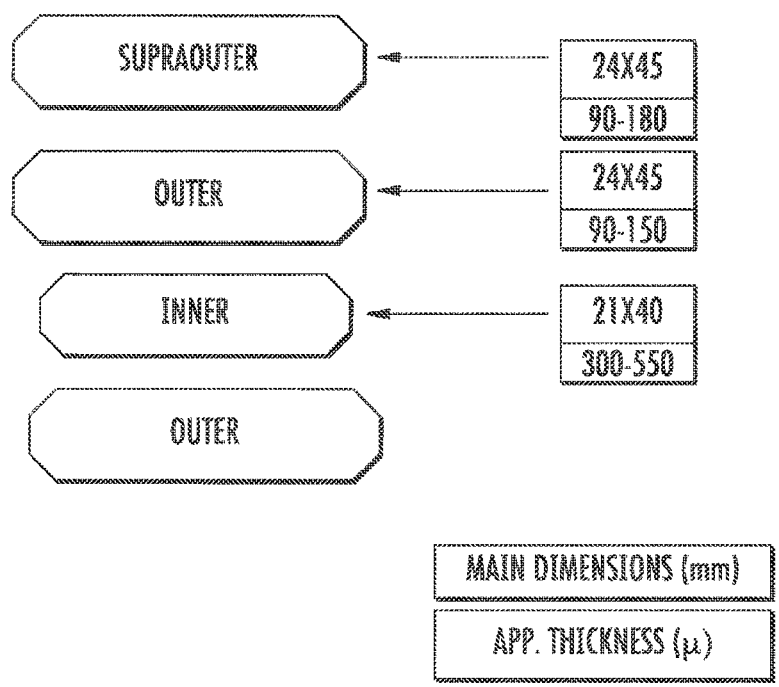
FIG. 3 shows the physical dimensions of the GRDF formulations shown in Example 11.
Figure 4:
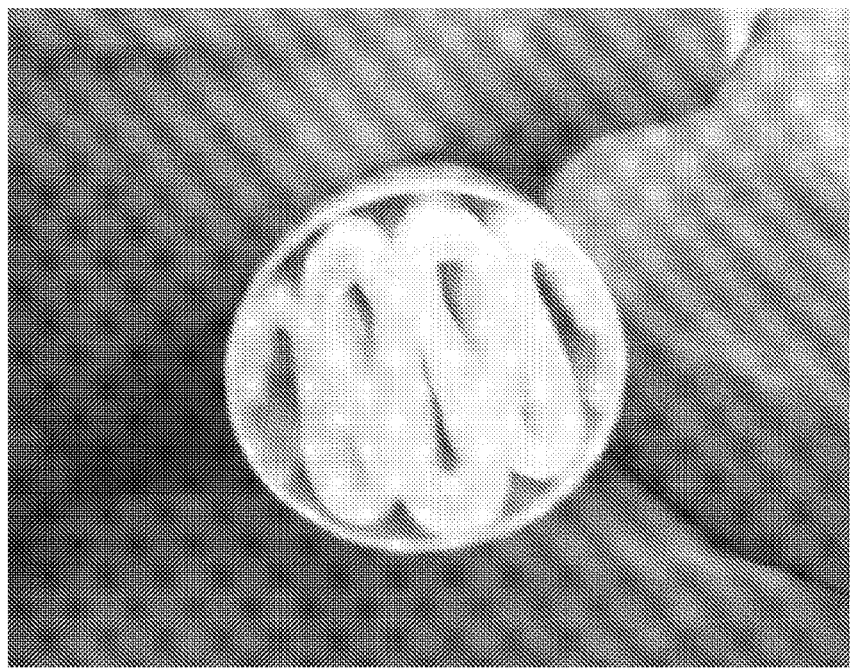
FIG. 4 shows a GRDF folded inside capsule prior to placing the capsule cap. Visible are the folds and their fold geometry.
Figure 6A:
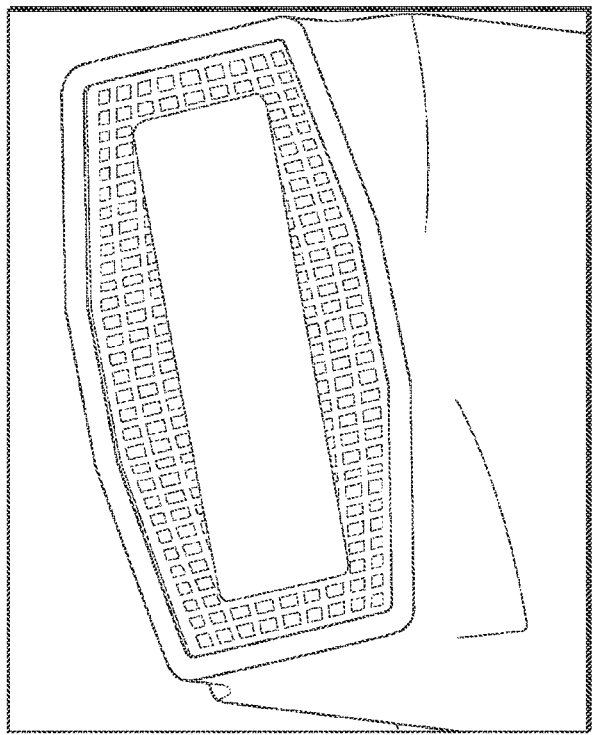
FIGS. 6A and 6B show the design of the anvil (A) and horn of (B) the ultrasound welding machine used for attaching the GRDF layers together.
Figure 6B:
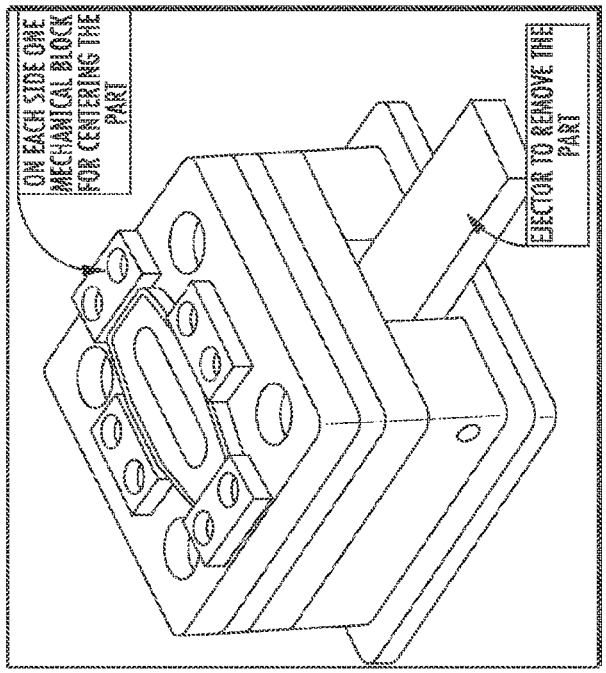
Figure 7A:
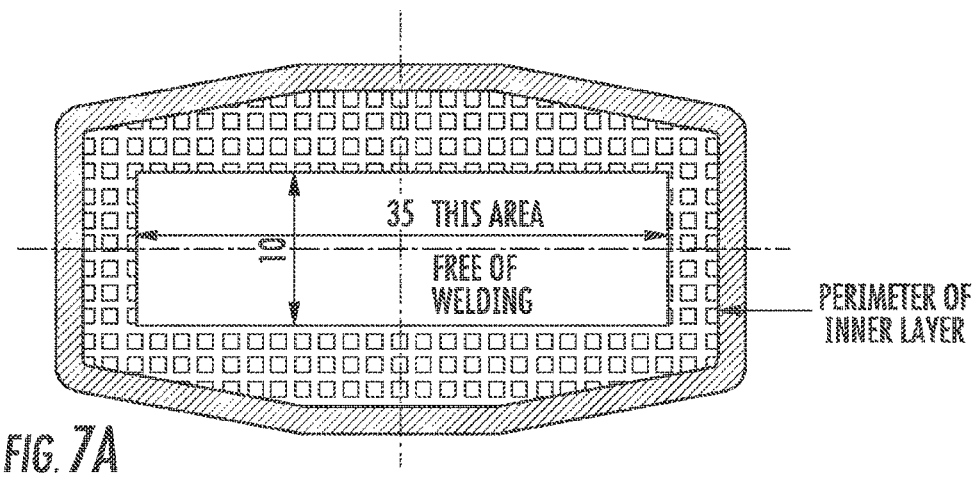
FIGS. 7A and 7B show a drawing of the ultrasound welding on the GRDF (A). The perimeter line of the internal layer is shown with an arrow and the extent of welding in a cross section of the GRDF is provided (B).
Figure 7B:
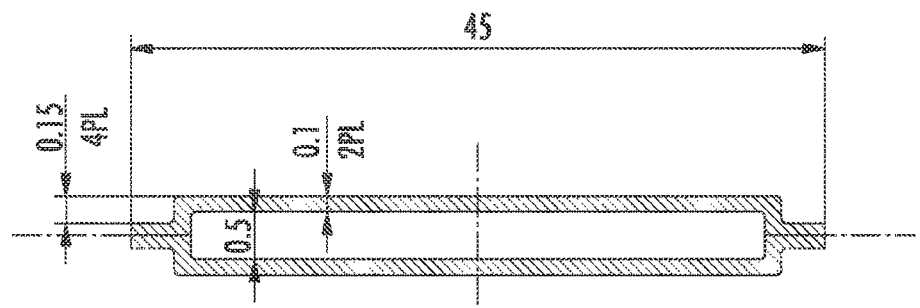

"Gastroretentive dosage form" as used herein refers to dosage forms with delayed gastric emptying as compared to food (or retention in the stomach beyond the retention of food).

"Simulated gastric fluid" and "Gastric medium", and "Simulated intestinal fluid" and "Intestinal medium", as used interchangeably herein refer to media, occurring in stomach and in intestines, correspondingly, or to the solutions that are used to mimic their chemical and/or enzymatic environment in vitro. One such media is described in Example 2.

The term "degradable" as used herein is intended as capable of being chemically and/or physically reduced, dissolved or broken down in the body of a patient and within a relevant time period.

The phrase "polymer which is not instantly soluble in gastric fluid" as used herein means that the polymer will gradually dissolve in the GI tract during its residence therein.

The term "inert" as used herein refers to components in the internal layer or compartment, outer membranes, optional layers and/or the immediate release layers that do not react with the active ingredient or affect its properties under normal conditions, or cause any biological effect upon administration to a subject.

The phrase "prolonged period" as used herein intends a period of delivery that lasts for several hours to about 24 hours, usually above 5 hours, and often between about 5 and 15 hours.

The terms "swellable" and "swelling" mean, with respect to a polymer, that the polymer is capable of imbibing fluid and expanding when in contact with fluid present in the environment of use.

The terms "active agent" and "drug" are used interchangeably herein and refer to an active pharmaceutical ingredient (API), compound, composition of matter or mixture thereof which provides a therapeutic or prophylactic effect.

A "patient" as referenced herein is a human or non-human mammal who may need to receive the gastroretentive drug formulations of the present invention.

"Treating" or "treatment", are used herein to refer to obtaining a desired pharmacological and physiological effect. The effect may be prophylactic in terms of preventing or partially preventing a disease, symptom or pathological condition and/or may be therapeutic in terms of a partial or complete cure of a disease, condition, symptom or adverse effect attributed to a pathological condition. Thus, "treatment" covers any treatment of a disease in a mammal, particularly a human, and includes: (a) preventing a pathological condition from occurring in an individual which may be predisposed to develop a pathological condition but has not yet been diagnosed as having it, i.e., causing the clinical symptoms of a pathological condition not to develop in a subject that may be predisposed to develop the condition but does not yet experience or display symptoms of the condition; (b) inhibiting, i.e., arresting or reducing the development of the pathological condition or its clinical symptoms; or (c) relieving symptoms associating with the pathological condition.

In the current embodiments, the gastroretentive drug delivery system includes an internal layer and an outer layer. The outer layer is formed from two films which are slightly larger than the internal layer and which are sealed or welded together around their perimeter and completely envelope the internal layer. Along with welding which connects the outer layers together, the outer portion of the internal layer is also welded to the outer layers.

Alternatively, in the current embodiments, the gastroretentive drug delivery system includes an internal layer and an outer layer, whereas the outer layer is formed from two membranes which are equal in size with the internal layer and which are sealed or welded together around their perimeter and the outer portion of the inner layer. Optionally the gastroretentive delivery system comprises an additional layer which is either larger or equal in size to the inner/outer membranes assembly, and envelops the assembly to prevent adhesion of the membranes onto themselves; the said layer can be formed with one or more membranes, ultrasonically welded or otherwise attached or affixed onto the assembly, and can optionally comprise an API. The ultrasonically welded or otherwise attached internal layer and outer layers are folded in an accordion arrangement and placed within a capsule. In some embodiments, the capsules are made from gelatin or hypromellose. The layers are shaped in essentially oval polygonal form such that they maximize the amount of space within the capsule that is filled. Once the gelatin or hypromellose capsule dissolves within the gastric medium, the internal layer and outer layers expand from the accordion folded orientation to a more planar orientation.

The gastroretentive drug formulations of the present invention markedly improve absorption and bioavailability of suitable active agents, and, in particular, ameliorate the absorption and bioavailability of drugs having a narrow window of absorption in the gastrointestinal tract, due to its ability to withstand peristalsis and mechanical contractility of the stomach, and consequently, release the drug in a controlled manner onto its absorption sites and without premature transit into non-absorbing regions of the GI tract. The inventors discovered that the gastroretentive drug formulation provides gastric retention of active agents having a narrow window of absorption for up to 24 hours under low or medium calorie diet, unlike other formulations in the art, that require high calorie and high fat diet for proper functioning. In addition, administration of these formulations to a mammal can improve the pharmacokinetic and pharmacodynamic properties of active agents having a narrow window of absorption. Since the gastroretentive drug formulations are fully degradable, they provide a means to administer the proper dose of the drug without generating non-degradable residues that would not be eliminated after drug release.

The gastroretentive drug formulations are stable, fully degradable and provide efficient delivery of various drugs in the gastrointestinal tract due to the combination of an internal layer having planar-accordion geometry where all components are fully biodegradable. The combination of swelling outer membrane layers with a substantially non-swelling internal layer having planar accordion geometry causes the internal layer to undergo an unfolding process once the formulation reaches the stomach, thus extending gastric residence time and preventing the dosage form from being evacuated until substantial or complete release.

Sustained-Release Gastroretentive Drug Formulations

In accordance with the first embodiment of the invention, a stable, degradable, multi-layered gastroretentive drug formulation for the sustained release of an active agent in the gastrointestinal tract is provided. The gastroretentive drug formulation comprises: i.) an internal layer or compartment comprising the active agent, one or more polymers and one or more modifying agents such as plasticizers and/or solubilizers and/or fillers; ii.) two outer membranes, each comprising at least one polymeric combination of hydrophilic polymer and a polymer insoluble in gastric media, and at least one plasticizer; and iii.) optionally an additional layer covering each outer membrane and comprising a powder or a film that prevents adherence of the outer membranes to itself.

In accordance with another embodiment of the invention, degradable, multi-layered gastroretentive drug formulation for the sustained release of an active agent can be combined with one or more immediate release layers covering the outer membranes and comprising the active agent and a polymer and optionally other excipients, known in the art, that provides for the immediate release of the active agent to form degradable, multi-layered gastroretentive drug formulation for combined immediate-release and sustained-release of the active agent. Optionally an additional layer covering each outer membrane and comprising a powder or a film that prevents adherence of the outer membranes to itself is included. Additional disclosure regarding the immediate and controlled release formulations are provided below.

Internal Layer

The internal layer or compartment in the gastroretentive drug formulations comprise the active agent and a polymer substantially uniformly distributed throughout the internal layer. The polymer can be a degradable hydrophilic polymer which is not instantly soluble in gastric fluid, a degradable enteric polymer which is substantially insoluble at pH less than 5.5, a hydrophobic polymer or mixtures thereof. It can further comprise acceptable pharmaceutical additives, such as plasticizers, humectants, fillers and others.

Examples of degradable hydrophilic polymers which are not instantly soluble in gastric fluid suitable for the invention are hydroxypropyl cellulose, hydroxypropylmethyl cellulose, polyvinyl pyrrolidone, polyethylene oxide and methylcellulose. Preferably, the enteric polymer is a polymethacrylate copolymers, cellulose acetate phthalate, hypromellose acetate succinate or hypromellose phthalate. These polymers are combined with active agent, such as Levodopa and/or Carbidopa. Exemplary ranges for active agents and polymers are provided the table below.

| Component | Range In Inner Layer |
|---|---|
| Carbidopa | 5-17% |
| Levodopa | 40-65% |
| Eudragit L100 | 10-35% |
| Poloxamer 407 | 7-19% |
| PEG 400 | 4-14% |

Preferably, the internal layer has planar accordion geometry. This feature, together with the presence of polymers as described above in the internal layer or compartment provides the internal layer with substantial mechanical strength. Preferably, the internal layer has a mechanical strength with Young's modulus of from about 0.5 to 15 Kgf/mm$^2$. Preferably, the range could be from about 3.0 to about 10.0 Kgf/mm$^2$ or from about 3.0 to about 6.0 Kgf/mm$^2$. The stress may range from about 0.03 to about 0.6 Kgf/mm$^2$ after 1 hour in simulated gastric fluid, such that the gastroretentive drug formulation reaches its maximum strength within one hour in simulated gastric fluid. Alternatively the range for stress may be from about 0.05 to about 0.4 Kgf/mm or about 0.1 to about 0.4 Kg/mm.

The components of the internal layer may be altered based on the characteristics of the active ingredients being delivered. For example, some ingredients may be more soluble in certain polymers than others and may require a reformulation of the internal layer. In some instances, the active ingredient may require a formulation of the internal layer that does not allow effective welding between the outer and internal layer. In such situations, the internal layer may be composed of the two or more portions, where each portion has definite function. In one instance, the central region (welding free) can be formulated as separate film to hold the active ingredient and be placed into the central portion and over the inner film comprising an additional portion that will support this central portion. This additional portion can then be welded to the outer layer. In another instance, whereas the internal layer cannot be formulated to develop the necessary mechanical strength in the gastric medium, at least one additional layer, optionally comprising no drug, could be used as a scaffold, whereupon the formulated drug reservoir film could be laid and welded or otherwise attached or affixed, onto one or both sides of said backbone, and the assembly could be welded to the outer membranes and other components of the delivery system.

Outer Membranes

Each of the outer membranes in the gastroretentive drug formulations comprises at least one polymeric combination of a hydrophilic polymer and a polymer, insoluble in gastric media, and at least one plasticizer.

Examples of suitable ingredients for the invention include gelatin, hydroxypropylcellulose, hydroxypropyl methylcellulose, pectin, polyethylene oxide, starch, and zein. Preferably, the hydrophilic polymer is gelatin. The amount of gelatin in each of the outer membranes is between about 20 and about 45% of the total outer membrane composition, and preferably between about 25 and about 35% of the total outer membrane composition.

Examples of enteric polymers that can be used in the outer membranes include hypromellose phthalate, hypromellose acetate succinate and polymethacrylate co-polymers. Preferably, the enteric polymer is polymethacrylate copolymer type A or polymethacrylate copolymer type C.

Plasticizers suitable for the invention include various polyethylene glycols, glycerin, triethylcitrate. Preferably, the plasticizer is propylene glycol.

The outer membranes swell in the presence of gastric fluid and are fully degradable within two hours in simulated intestinal fluid. The combination of swelling outer membrane layers with a non-swelling internal layer having planar accordion geometry causes the internal layer to undergo an unfolding process once the formulation reaches the stomach, thus extending gastric residence time and preventing the drug-containing dosage form from being evacuated until complete release. In one embodiment the internal layer has a swelling rate less than the swelling rate of the membrane.

The membrane permits passage of gastric medium from the environment to the internal layer and permits passage of the active agent from the internal layer through the membrane to the environment.

In some instances the kinetics of such transport can be unacceptably low. Therefore in some embodiments the outer membranes can be perforated with one or more orifices to facilitate the mass transfer processes through the membrane. In preferred embodiments the orifices are uniformly distributed over the area hereabout the formulated drug layer.

In a preferred embodiment, the outer layer does not contain any active ingredient. In other embodiments, the outer layer comprises one or more active ingredients.

Optional Additional Layer

The gastroretentive drug formulations of the invention may further comprise an optional additional layer covering each outer membrane and comprising a powder or a film. In some instances it may be found that the outer layers stick together in the capsule and do not unfold properly upon dissolving of the capsule. In such situations, this optional layer prevents adherence of the outer membranes to themselves and allows for the proper opening of the GRDF. In preferred embodiments, the optional layer comprises at least one powder, and optionally at least one polymer. In other embodiments the preferred polymers are rapidly-dissolving film formers, which can be selected from but not limited to soluble cellulose derivatives, i.e. methyl cellulose, hydroxypropyl cellulose, hydroxyethyl cellulose, hypromellose; various grades of povidone: polyvinyl alcohol and its derivatives, i.e. Kollicoat IR; soluble gums and others. The films may further comprise surface-active agents, plasticizers and humectants.

The Immediate Release Layers

The invention further contemplates gastroretentive drug formulations for combined immediate-release and controlled release of an active agent in the gastrointestinal tract. These formulations comprise an internal layer or compartment and at least two outer membranes as described above, and additionally comprise one or more immediate release layers covering the outer membranes and comprising the active agent and a soluble polymer that provides for the immediate release of the active agent. Examples of soluble polymers that can be used in the immediate release which can be selected from soluble cellulose derivatives, i.e. methyl cellulose, hydroxypropyl cellulose, hydroxyethyl cellulose, hypromellose; various grades of povidone; polyvinyl alcohol and its derivatives, i.e. Kollicoat IR; soluble gums and others. The films may further comprise surface-active agents, plasticizers and humectants, such as PEGs, different grades of polysorbates and sodium lauryl sulfate, for example.

The relative amounts of the polymers may be adjusted based on the solubility on the active ingredient.

While the internal layer and outer layer are generally welded together, the immediate release layer will not generally require such a strong connection with the rest of the GRDF device. Rather the immediate release formulation will quickly dissolve in order to deliver the drug of interest. The immediate release layer may be affixed to the outside of the GRDF using a compatible solvent, ultrasonic welding, or other means.

The ability to add an additional immediate release layer is particularly helpful in the development of GRDFs. By combining the immediate and controlled release nature of the current invention, one can alter the drug release profile for the drug of interest. Consequently, patients may receive both an immediate bolus of the drug as well as a prolonged delivery of the active agent with the purpose of establishing therapeutic levels of the drug quickly and maintaining these levels for prolonged period of time, up to 24 hour.

Of further note is the ability to deliver multiple drugs in the current GRDF. The current embodiments are not limited to the delivery of a single active pharmaceutical agent. Rather, multiple drugs may be formulated and delivered simultaneously. By combining the immediate and controlled release layers, multiple drugs may be simultaneously delivered with specific profiles. For example, a combined release formulation for levodopa/carbidopa is provided in the Examples.

All components of the internal layer or compartment, the outer membranes, the optional layers and/or the immediate release layers are pharmaceutically acceptable and inert.

Coating

As an additional method of delivering the immediate release of the drug, a coating may be applied to the capsule comprising the drug. Upon entry into the stomach, the coating will immediately allow release of the drug and enhance the release profile of the drug. Methods for applying coating to a capsule are well known to those of skill in the art.

Ultrasonic Welding

The internal layer or compartment, the outer membranes, the optional layers and/or the immediate release layers may be attached to each other by many means. Preferably, they are sealed by applying ultrasonic welding. One example of a device suitable for these purposes is the Dynamic 745 ultrasonic welder from Rinco Ultrasonics, but other devices may be employed. The welding effectively seals the internal layer within the outer layer by welding the outer layers together and also welding the perimeter of the internal layer to the outer layer. It can also efficiently attach the layers to one another without sealing a whole envelope, meaning that there is no need for same-material welding, should the formulations be compatible.

Different patterns and times may be used for the welding based on the needs of those skilled in the art. Although the periphery of the layers can be welded together, the current embodiments do not weld the central portion of the GRDF device so as to minimize any heating or effects on the majority of the internal layer which holds the active pharmaceutical agent for controlled release. In some situations it may be necessary to weld more of the internal layer based on the composition of the GRDF.

The GRDF Capabilities

The gastroretentive drug formulations are designed for oral administration and are compacted or folded into a standard size capsule which is easily swallowed. The active ingredient or ingredients is/are incorporated in the accordion pill as powders, grains, spheres, particles, microparticles, nanoparticles, multiparticulates, solid solutions, tablets or microcapsules. Active agents that may be delivered with the gastroretentive drug formulations include active agents which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, the digestion system, the histamine system and the central nervous system. Especially preferred are active agents used in the treatment of gastrointestinal diseases, including, but not limited to, duodenal ulcers, gastric ulcers. Zollinger-Ellison syndrome, gastroesophageal reflux disease, erosive esophagitis, gastritis, gastric carcinoma and spasticity. Other indications such as cancer, infections, and metabolic disorders are also envisioned in addition to other conditions known by those of skill in the art which may be addressed through gastroretentive device delivery.

Suitable active agents include, for example, proteins, enzymes, enzyme inhibitors, hormones, polynucleotides, nucleoproteins, polysaccharides, glycoproteins, lipoproteins, peptides, polypeptides, steroids, hypnotics and sedatives, psychic energizers, tranquilizers, anticonvulsants, antidepressants, muscle relaxants, antiparkinson agents, analgesics, immunosuppressants, anti-inflammatories, antihistamines, local anesthetics, muscle contractants, antimicrobials, antimalarials, antivirals, antibiotics, bronchodilators, anti-gout agents, antiobesity agents, antidiabetic agents, anti-hyper-cholesterol agents, hormonal agents including contraceptives, sympathomimetics, anti-hypertensive agents, diuretics, lipid regulating agents, ACE inhibitors, bismuth salts, synthetic prostaglandins, antiandrogenic agents, antiparasitics, neoplastics, antineoplastics, antihyperglycemics, hypoglycemics, nutritional agents and supplements, growth supplements, fats, ophthalmics, antienteritis agents, electrolytes and diagnostic agents.

Preferably, the active agent has a narrow window of absorption in the gastrointestinal tract. Antiviral, antifungal and antibiotic agents, including sulfonamides, quinolones, penicillins, cephalosporins, aminoglycosides, and tetracyclines, are representative classes of active agents that have a narrow window of absorption in the gastrointestinal tract. Specific examples of drugs include, but are not limited to, cimetidine, rantitidine, famotidine, nizatidine, zolentine, metronidazole, timidazole, amoxicillin, clarithromycin, minocyclinc, tetracycline, somatostatin analogues, including levodopa and carbidopa, In addition, active agent that act locally are, for example, drugs for the treatment of local infections, or drugs for the treatment of various gastrointestinal diseases and symptoms, or drugs for the treatment of metabolic disorders, for the treatment of local cancers or for the treatment of cancer related diseases. More specifically, the agents relevant in this aspect are these that have to be administered in the inflamed bowel, as occurs during inflammatory bowel diseases, such as metronidazole, vancomycin, budesonide and others, whose efficacy is impaired by unusually rapid emptying of the inflamed tissue. These materials can be poorly absorbed systemically, such as vancomycin, or could be incorporated into a targeted delivery system, such as for budesonide.

Other drugs that may be formulated according to the invention include drugs for the treatment of Parkinson's Disease. Parkinson's Disease (PD), one of the most common neurodegenerative diseases of the elderly, is a slowly progressive clinical syndrome characterized by resting tremor, slowness of movement, muscular rigidity, and gait instability. PD may also be accompanied by difficulty in swallowing, loss of olfactory sense, difficulty in speech, depression and dementia. The pathogenesis of PD involves degeneration of dopaminergic neurons in the substantia nigra pars compacta and a consequent depletion of the neurotransmitter dopamine in the basal ganglia. Since dopamine cannot cross the blood-brain barrier, Levodopa (LD) (which is enzymatically decarboxylated by the enzyme L-amino dopa decarboxylase in the CNS to dopamine), is used therapeutically to replenish the brain's diminished dopamine reservoir. LD is considered the most effective therapeutic drug for the treatment of Parkinson's disease. Decarboxylation reaction can also occur at some rate peripherally, even before levodopa reaches the brain. Therefore Levodopa is generally co-administered with an effective L-amino dopa decarboxylase inhibitor such as Carbidopa. The inhibition of Levodopa decarboxylation in the periphery reduces peripheral dopamine formation and decreases the side effects attributed to dopamine (i.e. orthostatic hypotension, nausea and vomiting), while simultaneously increasing the bioavailability of Levodopa to the CNS. Carbidopa/Levodopa is commercially available as a combination products, both as immediate-release (e.g. Sinemet®, Merck & Co., Inc.) or controlled-release (e.g. Sinemet-CR®, Merck & Co., Inc.) tablets.

The plasma half-life of LD is about 50 minutes, without Carbidopa (CD). When CD and LD are administered together, the half-life of LD is increased to about 1.5 hours. At steady state, the bioavailability of LD from Sinemet® tablets is approximately 99% relative to the concomitant administration of Carbidopa and LD.

Although LD is the most effective treatment for Parkinson's disease (PD), there are problems with its long term use. Early PD patients fair well with LD with a sustained response to each LD dose. Over time, however, the duration of the response after each dose declines, resulting in "wearing off", where the medication does not work until the next dose reaches therapeutic levels. As the disease progresses the patient suffers from longer OFF periods when the LD is not working. In addition, a disabling side effect of LD treatment is the occurrence of dyskinesias, usually as a peak dose effect. Both of these phenomena, wearing off and dyskinesias, are believed to be caused by the pulsatile stimulation of striatal dopamine receptors and the large difference between peak to trough levels of dopamine. It is beneficial, therefore, to provide continuous, rather then pulsatile, dopaminergic stimulation by either increasing the frequency of dosing or by treatment with a controlled release product. The current available controlled release LD treatment, Sinemet CR®, has shown decreased bioavailability and efficacy, since LD is absorbed mainly in the upper intestines and a slow release product that has passed the area of absorption will not be effective.

The GRDF formulations of the invention maintain controlled release of LD, that is retained at or above the area of absorption, the upper intestines, with minimal peak/trough variations, and thus provide the most beneficial treatment in terms of efficacy and safety profiles.

The gastroretentive dosage forms of this invention can conveniently release active agents in a sustained profile or in a combined immediate and sustained profile over a prolonged period, while maintaining high drug bioavailability for an extended period of time.

The detailed description of the present invention is further illustrated by the following examples, which are illustrative only and are not to be construed as limiting the scope of the invention. Variations and equivalents of these examples will be apparent to those skilled in the art in light of the present disclosure, the drawings and the claims herein.

Gastric Retention Under Low and Medium Calorie Diet

The gastroretentive drug formulations maintain their physical integrity over a prolonged period of time, such that the active agent is retained in the stomach for up to 24 hours under low or medium calorie diet. The use of a low and medium calorie diet is advantageous because it follows normal dietary habits of the patients and does not demand an excessive meal with each instance of dosing of the GRDF. Although the GRDF may be retained in the stomach for extended periods of time all of the GRDF components are degradable and undergo complete degradation once they reach the intestine.

The invention is further represented by the following examples. The examples are representative only and are not intended to limit the invention to the particular embodiments described therein.

EXAMPLES

Example 1

Ultrasonic Welding of GRDF

In order to weld the layers of the GRDF, the Dynamic 745 ultrasonic welder from Rinco Ultrasonics was used with the following parameters:

| Parameters of ultrasonic welding | |
|---|---|
| Trigger | 275 N |
| Rise of force Trigger | 380 N/s |
| Melting time | 650 ms |
| Rise of force Trigger | 600 N/s |
| Amplitude | 9 |
| Solidification force | 600 N |
| Holding time | 600 ms |

Figure 8:
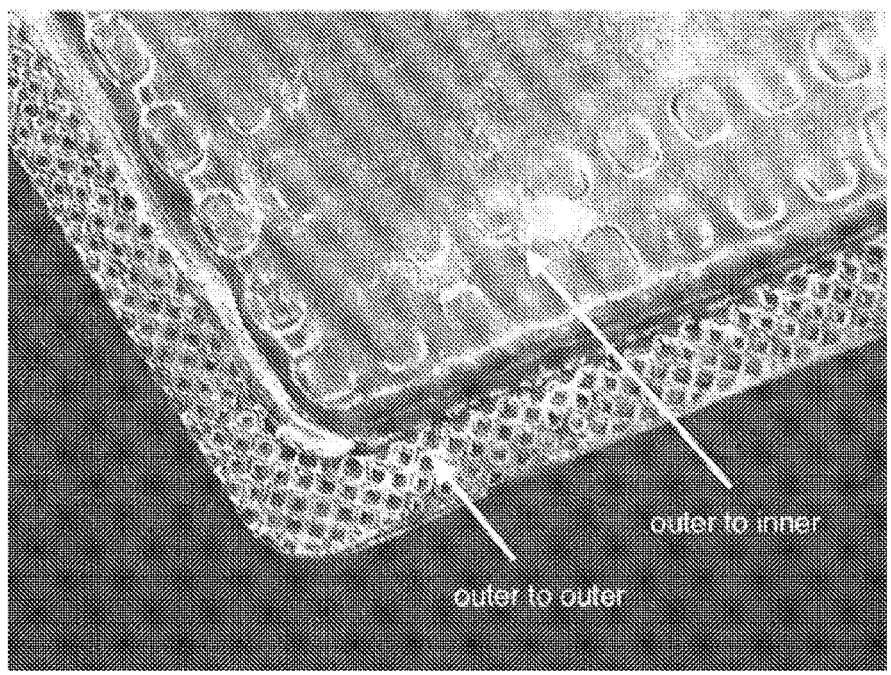
FIG. 8 shows a welded GRDF.

FIGS. 6A, 6B, 7A and 7B show the design of the anvil and horn of the ultrasonic welding machine used for attaching the GRDF layers together. In addition, a cross sectional view of the extent of the welded area is provided. FIG. 8 shows an enlarged photograph of a portion of a GRDF with the ultrasonic welding of the outer layers to each other forming an envelope around the internal layer. The welding between the peripheral portion of the internal layer with the outer layer is also visible.

Example 2

Unfolding of GRDF

The following data show that the GRDF of the current invention unfold within a short period of time and would not be quickly passed through the stomach before deployment and release of the active ingredients. The below experiments were conducted with a placebo GRDFs first loaded into capsules and then placed in either SGF pH 1.2 or acetate buffer (USP) pH 4.1 in a USP Apparatus 2, 50 rpm. GRDFs were visually inspected after 15 minutes. In addition, the lengths of the accordion laminates along its longest dimension were measured after 30, 60 and 120 minutes in the medium. Completely flat devices have a length of 45 mm. See FIGS. 10 and 11 for the results. The devices are unfolded by 30 minutes. Visual inspection at 15 minutes indicated that the pills were dissolved and the devices had opened to about the same size as seen at 30 minutes.

Example 3

Mechanical Properties of GRDF

The mechanical properties of the GRDFs and their films were tested. See FIG. 5 for results. Intact GRDFs, as well as specimens which were cut into a dog bone shape were tested in order to determine their mechanical properties. Values for the strain, load, stress, and Young's modulus are provided.

Example 4

Degradability of GRDF

The following results show the complete biodegradability of the GRDF of the current invention once it is passed into an environment similar to the intestinal tract. Four GRDF devices were placed in simulated intestinal fluid (USP SIF) and monitored every hour for three hours. The devices were not first loaded in a pill, but were placed directly into SIF. After three hours the devices dissolved.

Example 5

Carbidopa-Levodopa GRDF Formulation

A GRDF was manufactured using the following components for the internal layer, outer layers, and an immediate release layer.

| | Amount/GRDF (mg) | | | |
|---|---|---|---|---|
| Component | Internal layer | Outer (sum of two films) | Immediate Release Layer | Total |
| Carbidopa | 45.0 | | 30.0 | 75.0 |
| Levodopa | 200.0 | | 100.0 | 300.0 |
| Eudragit S100 | | 53.2 | | 53.2 |
| Eudragit L100 | 100.0 | 26.6 | | 126.6 |
| Eudragit L100-55 | | 26.6 | | 26.6 |
| Fish Gelatin | | 106.5 | | 106.5 |
| Propylene glycol | | 106.5 | | 106.5 |
| KOH | | 6.7 | | 6.7 |
| Poloxamer 407 | 65.0 | | | 65.0 |
| PEG 400 | 40.0 | | 8.3 | 48.3 |
| Methylcellulose | | | 4.7 | 4.7 |
| Povidone 90 | | | 18.4 | 18.4 |
| Total | 450 | 326.1 | 161.4 | 937.5 |

Example 6

Carbidopa-Levodopa GRDF Release Profiles

In order to illustrate the ability of the GRDF to provide both immediate release and controlled release of active ingredients, the release profile for the above (Example 5) Carbidopa/Levodopa GRDF was determined. Carbidopa and Levodopa are present in total amounts of 75 and 300 mg, respectively. Specifically, there are 30 mg Carbidopa in the immediate release layer and 45 mg in the internal layer which are provided to the patient as a controlled release. For Levodopa, 100 mg are in the immediate release layer and 200 mg in the internal layer.

Experiments were conducted in an acetate buffer (USP) pH 4.1 in a USP Apparatus 2, 50 rpm. As shown in FIG. 9, immediate release for both drugs occurred within 1 hour and extended release was seen for 8 hours.

These experiments illustrate the ability to effectively deliver a single or multiple drugs at the same time using the current GRDF. If delivered simultaneously, the drugs may be concentrated in the immediate release and controlled release layers to provide the desired profiles and release characteristics in one system.

Example 7

Carbidopa/Levodopa GRDF Pharmacokinetic Profiles Compared to Immediate Release Sinemet® and Controlled Release Sinemet CR® Pharmacokinetic Profiles in Healthy Subjects The Study A three-way crossover study was performed in healthy subjects to assess the pharmacokinetics of two single GRDF Levodopa/Carbidopa (LD/CD) dose formulations. A single dose of GRDF LD/CD containing Levodopa 300 mg and Carbidopa 75 mg (formulation in Example 5) administered to healthy male subjects after a light meal were compared with Sinemet® containing Levodopa 100 mg and Carbidopa 25 mg and Sinemet CR® containing Levodopa 200 mg and Carbidopa 50 mg.

Pharmacokinetics of Levodopa

The plasma half-life of Levodopa is about 50 minutes, without Carbidopa. When Carbidopa and Levodopa are administered together, the half-life of Levodopa is increased to about 1.5 hours. At steady state, the bioavailability of Carbidopa from Sinemet® tablets is approximately 99% relative to the concomitant administration of Carbidopa and Levodopa.

Carbidopa inhibits decarboxylation of peripheral Levodopa. It does not cross the blood-brain barrier and does not affect the metabolism of Levodopa within the central nervous system.

Carbidopa reduces the amount of Levodopa required to produce a given response by about 75 percent and, when administered with Levodopa, increases both plasma levels and the plasma half-life of Levodopa, and decreases plasma and urinary dopamine and homovanillic acid.

In clinical pharmacologic studies, simultaneous administration of Carbidopa and Levodopa produced greater urinary excretion of Levodopa in proportion to the excretion of dopamine than administration of the two drugs at separate times.

Patients treated with Levodopa therapy for Parkinson's Disease may develop motor fluctuations characterized by end-of-dose failure, peak dose dyskinesia, and akinesia. The advanced form of motor fluctuations ('on-off' phenomenon) is characterized by unpredictable swings from mobility to immobility. Although the causes of the motor fluctuations are not completely understood, in some patients they may be attenuated by treatment regimens that produce steady plasma levels of Levodopa.

A current formulation of Levodopa/Carbidopa (Sinemet CR®) provides controlled-release of ingredients over a 4- to 6-hour period. However, the sustained-release product of this combination is less systemically bioavailable (70 to 75%) than the immediate-release product (99%), and may require increased daily doses to achieve the same level of symptomatic relief. Typical starting doses of LD/CD are Levodopa 100 mg and Carbidopa 25 mg 3 or 4 times a day for a total of 300-400 mg Levodopa daily.

For the purpose of this study, the GRDF CD/LD 75/300 mg was planned for a 600 mg total daily dose of Levodopa.

Since gastric retention can be achieved by eating a high fat, high caloric meal (food retention), true gastric retention was assessed in healthy subjects that were administered a low calorie breakfast.

The Products
A. Reference Product

| | |
|---|---|
| Product | Sinemet ® |
| Dose Administered | 25/100 (1 tablet) |
| Active Ingredient | Carbidopa/Levodopa, immediate release |
| Dosage Form | Tablet |
| Strength | 100 mg/25 mg |
| Manufacturer | MERCK & CO., INC |

B. Reference Product

| | |
|---|---|
| Product | Sinemet CR ® |
| Dose Administered | 50/200 (1 tablet) |
| Active Ingredient | Carbidopa/Levodopa, controlled release |
| Dosage Form | Tablet |
| Strength | 25/100 mg |
| Manufacturer | MERCK & CO., INC |

C. Reference Product

| | |
|---|---|
| Product | GRDF CD/LD |
| Dose Administered | 75/300 mg |
| Active Ingredient | Carbidopa/Levodopa, controlled release |
| Dosage Form | capsule |
| Strength | 75/300 mg |

The Treatment

The single-center, open-label, single-dose, three way crossover, pharmacokinetic study was performed in 24 healthy male subjects between 18 and 55 years of age. Adult healthy subjects participated in 3 study days with at least 1 week washout period between days.

All oral formulations were swallowed whole with 240 ml water after a light breakfast. Standardized meals were given to all subjects throughout the study days.

Venous blood samples was drawn before dosing and then at frequent intervals to match the pharmacokinetic behavior of the drug. Levodopa plasma levels were analyzed.

The results of the study are shown in the Tables below and in FIG. 12:

| Levodopa Results | | | | | | | |
|---|---|---|---|---|---|---|---|
| | GRDF Lsmean | Sinemet IR Lsmean | Ratio | CV % | 90% CI Lo | 90% CI Hi | Significant |
| LnAUC | 5164 | 1218 | 4.238 | 11.58 | 4.008 | 4.482 | ** |
| LnCmax | 1400 | 624 | 2.243 | 20.42 | 2.034 | 2.474 | ** |
| LnMRT | 4.45 | 2.69 | 1.656 | 16.12 | 1.533 | 1.790 | ** |
| LnAUC_DA | 5164 | 3655 | 1.413 | | 1.336 | 1.494 | ** |
| LnCmax_DA | 1400 | 1873 | 0.748 | | 0.678 | 0.825 | ** |
| Tmax | 2.65 | 1.40 | 1.896 | | | | ** |
| | GRDF Lsmean | Sinemet CR Lsmean | Ratio | CV % | 90% CI Lo | 90% CI Hi | Significant |
| LnAUC | 5164 | 3104 | 1.664 | 11.58 | 1.573 | 1.761 | ** |
| LnCmax | 1400 | 1043 | 1.343 | 20.42 | 1.217 | 1.481 | ** |
| LnMRT | 4.45 | 3.54 | 1.259 | 16.12 | 1.165 | 1.360 | ** |
| LnAUC_DA | 5164 | 4655 | 1.109 | | 1.049 | 1.173 | ** |
| LnCmax_DA | 1400 | 1565 | 0.895 | | 0.812 | 0.987 | ** |
| Tmax | 2.65 | 2.17 | 1.221 | | | | ** |
| | CR Lsmean | IR Lsmean | Ratio | CV % | 90% CI Lo | 90% CI Hi | Significant |
| LnAUC | 3104 | 1218 | 2.547 | 11.58 | 2.409 | 2.694 | ** |
| LnCmax | 1043 | 624 | 1.671 | 20.42 | 1.515 | 1.843 | ** |

-continued

| Levodopa Results | | | | | | | |
|---|---|---|---|---|---|---|---|
| LnMRT | 3.54 | 2.69 | 1.316 | 16.12 | 1.218 | 1.422 | ** |
| LnAUC_DA | 4655 | 3655 | 1.274 | | 1.204 | 1.347 | ** |
| LnCmax_DA | 1565 | 1873 | 0.836 | | 0.758 | 0.922 | ** |
| Tmax | 2.17 | 1.40 | 1.552 | | | | ** |

For log-transformed data (Ln) the LSmeans are geometric means and ratios are geometric mean ratios.
AUC = AUC 0-t
MRT = Mean Residence Time (hours)
_DA = Indicates Parameter Was Dose-Adjusted to 300 mg
CV % = Estimated Within-Subject Coefficient of Variation
** = $p < 0.05$, blank entry indicates $p > 0.05$ (adjusted for multiple pairwise comparisons)

The results show that the GRDF LD/CD, compared to the reference products, extended retention time in the stomach and controlled release of the active ingredients over a 5-hour period. GRDF LD/CD provided prolonged release of the active ingredients at a site above their absorption window and improved bioavailability with fewer variations in plasma levels, thus providing steady plasma levels of Levodopa and Carbodopa.

It is known that patients treated with Levodopa therapy for Parkinson's Disease may develop motor fluctuations characterized by end-of-dose failure, peak dose dyskinesia, and akinesia. These symptoms may be attenuated by treatment regimens that produce steady plasma levels of Levodopa. By providing a quick rise, yet steady level of Levodopa and Carbodopa, the GRDF LD/CD satisfy the need for a combination of immediate release and controlled release mechanism of LD/CD that provide steady plasma levels of Levodopa and Carbodopa, thus resulting in fewer doses per day and better patient response and compliance.

Example 8

Effect of GRDF Formulations on Gastric Retention in Healthy Subjects and in Parkinson Patients To determine the effect of GRDF formulations on gastric retention clinical trials were performed with various placebo GRDFs using MRI. The drug reservoir layer of the GRDF for these studies does not contain an active ingredient. Instead, the drug reservoir contains iron oxide food coloring (sicovit black e172) that can be visualized in a magnetic resonance imaging (MRI).

Results of these MRI studies showed that in healthy volunteers the GRDF formulations were retained in the stomach for 7-13 hours and for 7-24 hours in Parkinson patients.

Example 9

Carbidopa-Levodopa GRDF Formulation

Three additional GRDF formulations were manufactured.

| | mg per GRDF |
|---|---|
| Levodopa | 200.0 |
| Carbidopa | 50.0 |
| KOH | 6.0 |
| Propylene glycol | 94.2 |
| Gelatin (Fish) | 94.2 |
| Eudragit L100-55 | 23.5 |
| Eudragit L100 | 184.4 |
| Eudragit S100 | 47.1 |
| PEG 400 | 13.1 |
| Tween 80 | 11.8 |
| Povidone (Kollidon)90F | 13.7 |
| Lutrol F127 (Poloxamer 407) | 89.3 |
| Total | 827.3 |
| Levodopa | 300.0 |
| Carbidopa | 75.0 |
| KOH | 6.0 |
| Propylene glycol | 94.2 |
| Gelatin (Fish) | 94.2 |
| Eudragit L100-55 | 23.5 |
| Eudragit L100 | 83.9 |
| Eudragit S100 | 47.1 |
| PEG 400 | 43.5 |
| Tween 80 | 14.7 |
| Povidone (Kollidon)90F | 14.7 |
| Lutrol F127 (Poloxamer 407) | 30.3 |
| HPMCP 55 | 32.4 |
| HPMCP 55 S | 32.4 |
| Total | 827.0 |
| Levodopa | 300.0 |
| Carbidopa | 75.0 |
| KOH | 6.0 |
| Propylene glycol | 94.2 |
| Gelatin (Fish) | 94.2 |
| Eudragit L100-55 | 23.5 |
| Eudragit L100 | 93.7 |
| Eudragit S100 | 47.1 |
| PEG 400 | 43.4 |
| Tween 80 | 14.7 |
| Povidone (Kollidon)90F | 14.7 |
| Lutrol F127 (Poloxamer 407) | 30.2 |
| HPMCP 55 | 32.4 |
| HPMCP 55 S | 32.4 |
| Total | 836.8 |

Example 10

Carbidopa/Levodopa GRDF Immediate and Controlled Release Profiles Compared to Immediate Release Sinemet® and Controlled Release Sinemet CR® Pharmacokinetic Profiles in Healthy Subjects The Objectives of the Study The aim of this study was to evaluate the GRDF CD/LD optimal profile, by comparing the pharmacokinetic profiles of Levodopa and Carbidopa, following oral administration of a single-dose of the three different controlled-release GRDF CD/LD formulations (Example 9) with differing ranges of release profiles, with the pharmacokinetic profiles of a single-dose of the reference formulation, Sinemet®

50/200 mg given as two 25/100 mg IR tablets. An additional objective was to monitor subjects for adverse events during the study period and to compare the safety of the test formulations with the reference formulation.

Study Design

The study was designed as a single center, randomized, single-dose, open label, four-way, four-treatment, comparative crossover study. The study included four identical dosing periods, with each period including a Carbidopa pre-treatment day and a study-drug dosing day, during which a single dose of either one of the test formulations or reference drug was administered after a light-medium breakfast. Administration was followed by pharmacokinetic blood sampling and adverse event monitoring for the next 24 hours. A single dose of GRDF CD/LD with Levodopa either 200 or 300 mg and Carbidopa either 50 or 75 mg was administered to twenty four (24) healthy male subjects aged 18-55 (inclusive) after a light meal. The GRDF CD/LD was planned for a bid dosing schedule for a total daily dose of 400-600 mg per day of Levodopa. The GRDF CD/LD was formulated to release its two active ingredients as a combination of immediate release and controlled release mechanisms to provide quick yet steady levels of Levodopa. This study tested the pharmacokinetics of the gastric retentive controlled release GRDF CD/LD after a low-medium calorie breakfast with a low protein content since protein competes with Levodopa absorption.

| The Products | |
|---|---|
| Test Product | GRDF CD/LD |
| Doses Administered | 75/300 mg, or 50/200 mg |
| Active Ingredient | Carbidopa/Levodopa, IR + CR |
| Dosage Form | capsule |

The 75/300 mg dose was tested in two formulations (a and b), the 50/200 mg dose was in one formulation.

| | |
|---|---|
| Reference Product | Sinemet ® tablet (Carbidopa/Levodopa 25/100 mg) |
| Dose Administered | 50 mg carbidopa and 200 mg levodopa (2 tablets of 25/100 mg) |
| Active Ingredient | Carbidopa/Levodopa, immediate release |
| Dosage Form | Tablet |
| Manufacturer | MERCK & CO., INC |
| Carbidopa Pretreatment | Lodosyn ® |
| Dose Administered | 50 mg (2 tablet) 3 times on Day (−1) |
| Active Ingredient | Carbidopa |
| Dosage Form | Tablet |
| Manufacturer | MERCK & CO., INC |

The subjects were randomly assigned to a unique treatment sequence.

Study Procedures

The study drugs were swallowed whole with 240 ml of water at room temperature. Each subject was exposed to a washout period of at least 7 days between treatments.

For measurement of Carbidopa and Levodopa plasma levels, for each of the study periods, 17 serial blood samples were collected per subject. The pharmacokinetic data of Levodopa were evaluated.

Levodopa Results

Figure 13:
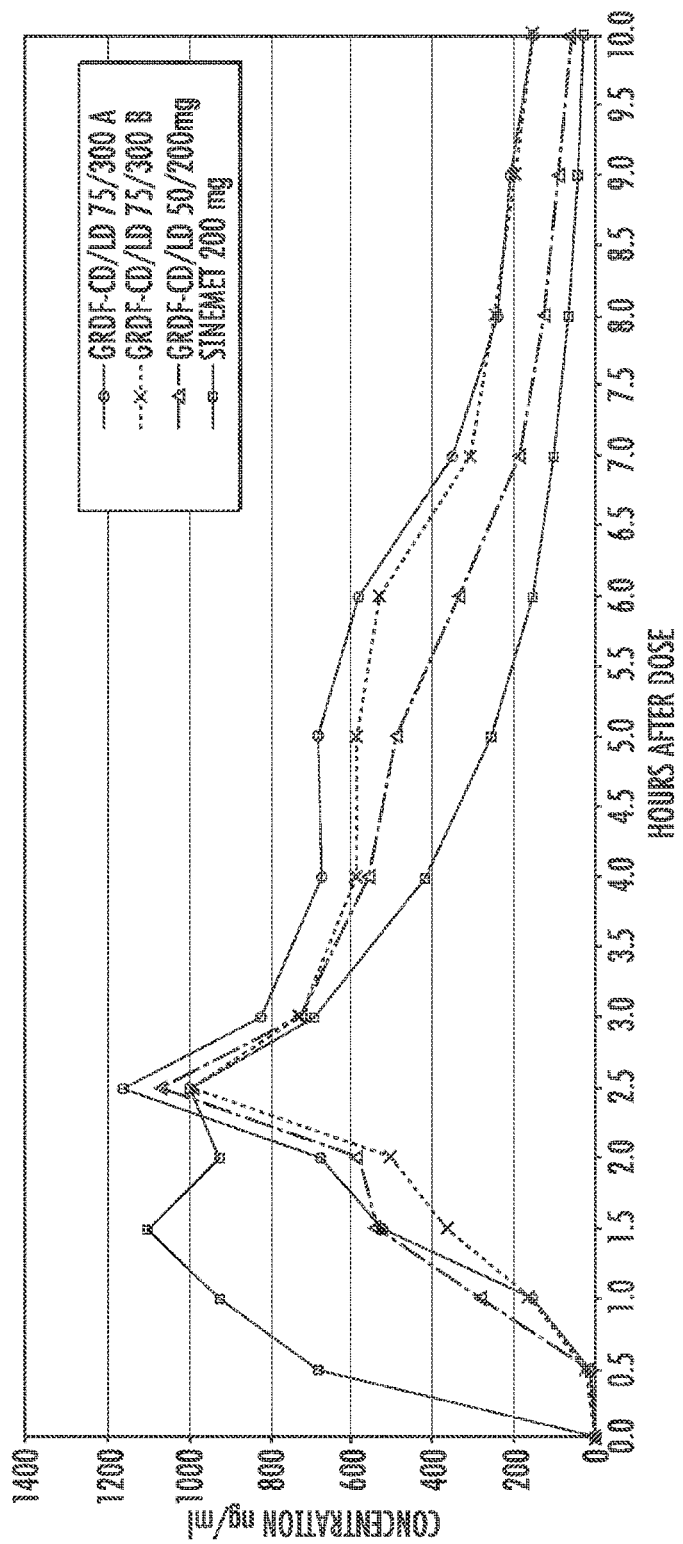
FIG. 13 shows the Levodopa Least-Squares Mean Concentrations in blood samples versus time in subjects treated with GRDF CD/LD 75/300 mg; GRDF CD/LD) 50/200) mg; and Sinemet® IR CD/LD 50/200 mg, as described in Example 10.

The Levodopa results of 21 volunteers are shown in FIG. 13 in the Tables below:

| | Least-Squares Means (N = 21) | | | |
|---|---|---|---|---|
| | GRDF CD/LD 75/300 A | GRDF CD/LD 75/300 B | GRDF CD/LD 50/200 | Sinemet ® (2 × 100 mg) |
| AUC 0-t | 5291 | 5216 | 3732 | 3886 |
| AUC 0-inf | 5650 | 5545 | 3828 | 3945 |
| Cmax | 1240 | 1076 | 1116 | 1424 |
| Tmax | 2.60 | 2.74 | 2.51 | 1.37 |
| MRT 0-t | 5.56 | 6.64 | 4.14 | 2.80 |
| MRT 0-inf | 5.96 | 7.20 | 4.35 | 2.97 |

| | Ratios of Least Squares Means | | | | |
|---|---|---|---|---|---|
| | GRDF 300A/ GRDF 300B | GRDF 300A/ GRDF 200 mg | GRDF 300A/Sinemet ® | GRDF 300B/GRDF 200 mg | GRDF 300B/ Sinemet ® |
| AUC 0-inf | 1.014 | 1.418 | 1.362 | 1.398 | 1.342 |
| Cmax | 1.019 | 1.476 | 1.432 | 1.449 | 1.406 |
| Tmax | 1.153 | 1.111 | 0.871 | 0.964 | 0.756 |
| MRT 0-t | 0.673 | 1.690 | 1.801 | 2.509 | 2.674 |
| MRT 0-inf | 0.837 | 1.342 | 1.989 | 1.602 | 2.376 |
| AUC 0-t | 0.828 | 1.370 | 2.010 | 1.654 | 2.427 |

| | 90% Confidence Intervals on Least-Squares Geometric Mean Ratios | | | | |
|---|---|---|---|---|---|
| | GRDF 300A/GRDF 300B | GRDF 300A/GRDF 200 mg | GRDF 300A/Sinemet ® | GRDF 300B/GRDF 200 mg | GRDF 300B/ Sinemet ® |
| AUC 0-t | | | | | |
| 90% CI Low | 0.968 | 1.353 | 1.294 | 1.330 | 1.271 |
| 90% CI Hi | 1.070 | 1.495 | 1.429 | 1.470 | 1.405 |
| AUC 0-inf | | | | | |
| 90% CI Low | 0.931 | 1.348 | 1.303 | 1.344 | 1.298 |
| 90% CI Hi | 1.100 | 1.577 | 1.520 | 1.545 | 1.489 |

| 90% Confidence Intervals on Least-Squares Geometric Mean Ratios | | | | |
|---|---|---|---|---|
| GRDF 300A/GRDF 300B | GRDF 300A/GRDF 200 mg | GRDF 300A/Sinemet ® | GRDF 300B/GRDF 200 mg | GRDF 300B/ Sinemet ® |

Cmax

| | | | | | |
|---|---|---|---|---|---|
| 90% CI Low | 1.029 | 0.965 | 0.751 | 0.829 | 0.646 |
| 90% CI Hi | 1.314 | 1.232 | 0.959 | 1.059 | 0.824 |

The results indicate that gastroretentive controlled-release delivery of levodopa yields true controlled-release behavior Both gastroretentive formulations have shown comparable bioavailability, slightly inferior to lower-doses GRDFs, and to the immediate-release formulation, as expected. The mean residence times are increased in gastroretentive controlled-release products in comparison with immediate-release formulation, two-fold and higher. The lack of proportionality of Cmax in correlation to the dose is evident, and consistent with true controlled-release behavior.

Example 11

Carbidopa-Levodopa GRDF Formulation

Two additional GRDF formulations was manufactured using the following components for the internal layer, outer layers, and an immediate release layer.

| Accordion pill Carbidopa/Levodopa 50/250 mg Amount/GRDF (mg) | | | | |
|---|---|---|---|---|
| Component | Internal layer | Outer (sum of two films) | Immediate Release Layer | Total |
| Carbidopa | 25.0 | | 25.0 | 50.0 |
| Levodopa | 180.0 | | 70.0 | 250.0 |
| Eudragit S100 | | 47.1 | | 47.1 |
| Eudragit L100 | 61.0 | 23.5 | | 84.5 |
| Eudragit L100-55 | | 23.5 | | 23.5 |
| Fish Gelatin | | 94.2 | | 94.2 |
| Propylene glycol | | 94.2 | | 94.2 |
| KOH | | 6.0 | | 6.0 |
| Poloxamer 407 | 32.0 | | | 32.0 |
| PEG 400 | 30.0 | | 3.1 | 33.1 |
| Tween 80 | | | 11.8 | 11.8 |
| Povidone 90 | | | 13.7 | 13.7 |
| Total | 328.0 | 288.5 | 123.6 | 740.1 |

| Accordion pill Carbidopa/Levodopa 50/375 mg Amount/GRDF (mg) | | | | |
|---|---|---|---|---|
| Component | Internal layer | Outer (sum of two films) | Immediate Release Layer | Total |
| Carbidopa | 25.0 | | 25.0 | 50.0 |
| Levodopa | 275.0 | | 100.0 | 375.0 |
| Eudragit S100 | | 47.1 | | 47.1 |
| Eudragit L100 | 80.8 | 23.5 | | 104.3 |
| Eudragit L100-55 | | 23.5 | | 23.5 |
| Fish Gelatin | | 94.2 | | 94.2 |
| Propylene glycol | | 94.2 | | 94.2 |
| KOH | | 6.0 | | 6.0 |
| Poloxamer 407 | 45.1 | | | 45.1 |
| PEG 400 | 40.4 | | 3.9 | 44.3 |
| Tween 80 | | | 14.7 | 14.7 |
| Povidone 90 | | | 14.7 | 14.7 |
| Total | 466.3 | 288.5 | 158.3 | 913.1 |

Example 12

Carbidopa-Levodopa GRDF Release Profiles

In order to illustrate the ability of the GRDF to provide both immediate release and controlled release of active ingredients, the release profile for the above two Carbidopa/Levodopa GRDF was determined. Carbidopa and Levodopa are present in total amounts of 50 and 250 or 50 and 375 mg, respectively (Example 11). Specifically, there are 25 mg Carbidopa in the immediate release layer and 25 mg in the internal layer which are provided to the patient as a controlled release. For Levodopa, 70 or 100 mg are in the immediate release layer and 180 or 275 mg in the internal layer.

Experiments were conducted in an acetate buffer (USP) pH 4.1 in a USP Apparatus 2, 50 rpm. Immediate release for both drugs occurred within 1 hour and extended release was seen for 12 hours for the 250 mg Levodopa formulation and 16 hours for the 375 mg Levodopa formulation.

The invention claimed is:

1. A gastro-retentive agent delivery device for oral intake, the device configured for unfolding from a folded configuration for oral intake to an unfolded configuration for gastric retention, the device comprising:
   a first outer membrane and a second outer membrane sandwiching an internal layer therebetween;
   the internal layer being different from said first outer membrane and from said second outer membrane;
   the internal layer comprising a first active agent distributed therein;
   the internal layer being configured for imparting mechanical strength to the device sufficient to enable, upon unfolding of the device, the preservation of said unfolded configuration to provide gastric retention;
   at least one first immediate release layer, overlying said first outer membrane, said at least one first immediate release layer being different from said outer membrane and from said internal layer, said at least one first immediate release layer comprising a respective second active agent, the at least one first immediate release layer configured for providing immediate release of the respective second active agent in the stomach;

wherein said first active agent and said respective second active agent are the same or different;

wherein in the folded configuration the device is sufficiently compact to be placed within a capsule dissolvable within the stomach.

2. The device according to claim 1, further comprising at least one second immediate release layer, overlying said second outer membrane, and comprising a respective third active agent, the at least one second immediate release layer configured for providing immediate release of the respective third active agent in the stomach, wherein said respective third active agent and said respective second active agent and said first active agent are the same or different.

3. The device according to claim 1, wherein in the folded configuration the internal layer and the two outer membranes and the at least one first immediate release layer are arranged in accordion folded configuration.

4. The device according to claim 2, wherein in the folded configuration the internal layer, the two outer membranes, the at least one first immediate release layer, and the at least one second immediate release layer are arranged in accordion folded configuration.

5. The device according to claim 1, wherein said outer membranes and said internal layer are degradable in the intestine.

6. The device according to claim 1, wherein said at least one first immediate release layer is degradable in the stomach.

7. The device according to claim 2, wherein said at least one first immediate release layer and said at least one second immediate release layer are degradable in the stomach.

8. The device according to claim 1, wherein said first active agent is any one of levodopa, carbidopa or levodopa/carbidopa mixture.

9. The device according to claim 1, wherein said respective second active agent is any one of levodopa, carbidopa or levodopa/carbidopa mixture.

10. The device according to claim 2, wherein said respective third active agent is any one of levodopa, carbidopa or levodopa/carbidopa mixture.

11. The device according to claim 8, wherein said respective second active agent is any one of levodopa, carbidopa or levodopa/carbidopa mixture.

12. The device according to claim 11, wherein said respective third active agent is any one of levodopa, carbidopa or levodopa/carbidopa mixture.

13. The device according to claim 1, wherein said internal layer comprises at least one polymer.

14. The device according to claim 13, wherein said at least one polymer comprises at least a polymer not instantly soluble in a gastric content.

15. The device according to claim 14, wherein said polymer not instantly soluble in a gastric content is an enteric polymer or a non-enteric insoluble polymer.

16. The device according to claim 14, further comprising at least one polymer soluble in a gastric content.

17. The device according to claim 1, the internal layer further comprising a plasticizer.

18. The device according to claim 1, wherein each of said two outer membranes comprises a polymer and a plasticizer, said polymer comprised in each of said two outer membranes being any one of a hydrogel, a non-hydrogel, or a combination thereof.

19. The device according to claim 16, wherein said polymer soluble in gastric content is a hydrogel, and wherein said hydrogel is any one of proteins, polysaccharides, gelatin, polydextrose, hydroxypropyl cellulose, hypromellose, hydroxyethyl methyl cellulose, hydroxyethyl cellulose, methyl cellulose, polyethylene oxide, polyvinyl alcohol, or any combination of two or more of the above.

20. The device according to claim 16, wherein said polymer is a hydrogel, being any one of gelatin, hydroxypropyl cellulose or hypromellose.

21. The device according to claim 14, wherein said polymer not instantly soluble in a gastric content is an enteric polymer, and wherein said enteric polymer is any one of shellac, cellacefate, hypromellose phthalate, hydroxypropyl methylcellulose acetate succinate, polyvinyl acetate phthalate, aliginic acid, carboxymethyl cellulose, a polymethacrylate copolymer, the salts of the above or a combination of two or more of the above.

22. The device according to claim 1, wherein said at least one first immediate release layer comprises at least one polymer.

23. The device according to claim 13, wherein the internal layer comprises said first active agent and said at least one polymer substantially uniformly distributed throughout the internal layer.

24. The device according to claim 1, further comprising said capsule, and wherein in the folded configuration the device is accommodated within said capsule.

25. The device according to claim 1, wherein said at least one first immediate release layer comprises said second active agent and a soluble polymer that provides for the immediate release of said second active agent.

26. The device according to claim 2, wherein said at least one second immediate release layer comprises said third active agent and a soluble polymer that provides for the immediate release of said third active agent.

* * * * *